United States Patent [19]

Nishida et al.

[11] Patent Number: 4,879,292
[45] Date of Patent: Nov. 7, 1989

[54] CERTAIN-PHENOXY-PHENOXY-ALKYLENE-OXY-PYRIMIDINES OR SYMMETRICAL TRIAZINES, THIO-ANALOGUES THEREOF, HAVING INSECTICIDAL ACTIVITY

[75] Inventors: Sumio Nishida; Noritada Matsuo, both of Hyogo; Makoto Hatakoshi, Osaka; Hirosi Kisida, Hyogo, all of Japan

[73] Assignee: Sumitomo Chemical Company, Limited, Osaka, Japan

[21] Appl. No.: 171,851

[22] Filed: Mar. 22, 1988

Related U.S. Application Data

[60] Division of Ser. No. 40,796, Apr. 21, 1987, Pat. No. 4,751,225, which is a continuation of Ser. No. 601,284, Apr. 17, 1984, abandoned.

[30] Foreign Application Priority Data

Apr. 25, 1983 [JP] Japan .................................. 59-73400

[51] Int. Cl.$^4$ ................. C07D 239/30; C07D 251/28; A01N 43/54; A01N 43/66
[52] U.S. Cl. .................................... 514/241; 544/211; 544/218; 544/219; 544/315; 544/317; 546/301; 548/186; 568/635; 568/636; 568/637; 568/638
[58] Field of Search ................ 546/301; 544/218, 219, 544/315, 317, 211; 514/241, 256

[56] References Cited

U.S. PATENT DOCUMENTS 4,770,691 9/1988 Nezu et al. ............................... 71/92

Primary Examiner—Alan L. Rotman
Attorney, Agent, or Firm—Birch, Stewart, Kolasch & Birch

[57] ABSTRACT

A nitrogen-containing heterocyclic compound of the formula:

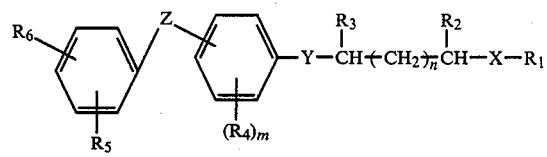

wherein
$R_1$ is either one of the following groups:

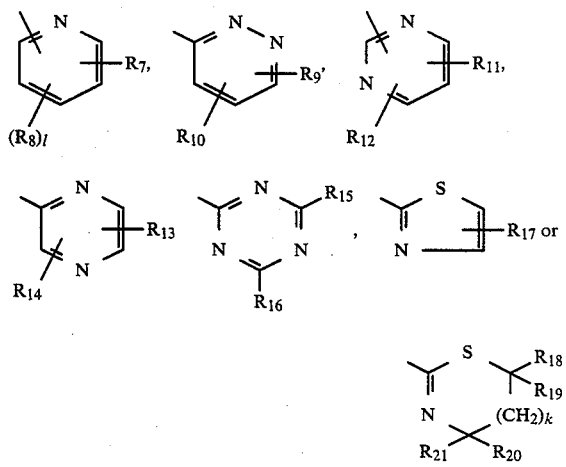

(in which $R_7$, $R_8$, $R_9$, $R_{10}$, $R_{11}$, $R_{12}$, $R_{13}$, $R_{14}$, $R_{15}$, $R_{16}$ and $R_{17}$ are, the same or different, each a hydrogen atom, a halogen atom, a $C_1$-$C_4$ alkyl group, a $C_1$-$C_4$ alkoxy group, a $C_1$-$C_4$ alkylthio group, a trifluoromethyl group or a nitro group, $R_{18}$, $R_{19}$, $R_{20}$ and $R_{21}$ are, the same or different, each a hydrogen atom or a methyl group, k is an integer of 0 to 1 and l is an integer of 0 to 3);
$R_2$ and $R_3$ are, the same or differnt, each a hydrogen atom, a halogen atom or a methyl group;
$R_4$ is a halogen atom or a methyl group;
$R_5$ and $R_6$ are, the same or different, each a hydrogen atom, a halogen atom, a $C_1$-$C_4$ alkyl group, a $C_1$-$C_4$ alkoxy group, a $C_1$-$C_4$ haloalkyl group or a $C_1$-$C_4$ haloalkoxy group;
X, Y and Z are, the same or different, each an oxygen atom, a sulfur atom or a methylene group;
m is an integer of 0 to 4; and
n is an integer of 0 to 2,
which is useful as an insecticidal agent.

37 Claims, No Drawings

CERTAIN-PHENOXY-PHENOXY-ALKYLENE-OXY-PYRIMIDINES OR SYMMETRICAL TRIAZINES, THIO-ANALOGUES THEREOF, HAVING INSECTICIDAL ACTIVITY

This application is a divisional of copending application Ser. No. 040,796, filed on Apr. 21, 1987, now U.S. Pat. No. 4,751,225 which is a continuation of application Ser. No. 601,284, filed on Apr. 17, 1984 (now abandoned).

The present invention relates to nitrogen-containing heterocyclic compounds, and their production and use.

Said nitrogen-containing heterocyclic compounds are representable by the formula:

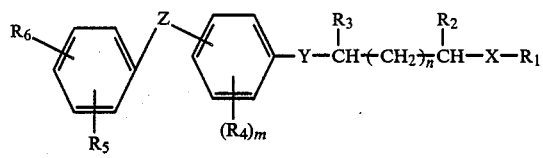

wherein
$R_1$ is either one of the following groups:

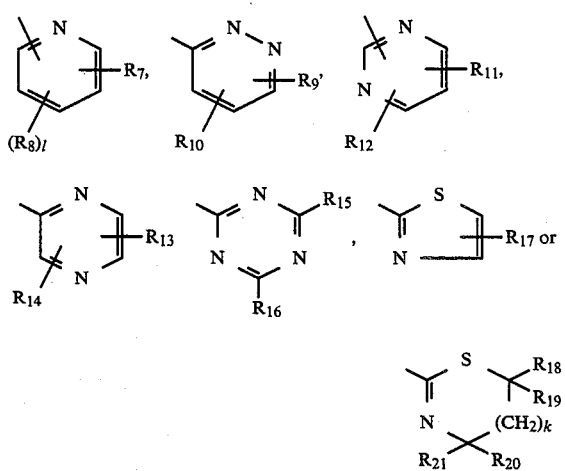

(in which $R_7$, $R_8$, $R_9$, $R_{10}$, $R_{11}$, $R_{12}$, $R_{13}$, $R_{14}$, $R_{15}$, $R_{16}$ and $R_{17}$ are, the same or different, each a hydrogen atom, a halogen atom, a $C_1$-$C_4$ alkyl group, a $C_1$-$C_4$ alkoxy group, a $C_1$-$C_4$ alkylthio group, a trifluoromethyl group or a nitro group, $R_{18}$, $R_{19}$, $R_{20}$ and $R_{21}$ are, the same or different, each a hydrogen atom or a methyl group, k is an integer of 0 to 1 and l is an integer of 0 to 3);
$R_2$ and $R_3$ are, the same or different, each a hydrogen atom, a halogen atom or a methyl group;
$R_4$ is a halogen atom or a methyl group;
$R_5$ and $R_6$ are, the same or different, each a hydrogen atom, a halogen atom, a $C_1$-$C_4$ alkyl group, a $C_1$-$C_4$ alkoxy group, a $C_1$-$C_4$ haloalkyl group or a $C_1$-$C_4$ haloalkoxy group;
X, Y and Z are, the same or different, each an oxygen atom, a sulfur atom or a methylene group;
m is an integer of 0 to 4; and
n is an integer of 0 to 2.

In the above significances, the term "halogen" includes chlorine, bromine, iodine and fluorine.

Among the nitrogen-containing heterocyclic compounds, preferred are those of the formula (I) wherein $R_1$ is either one of the following groups:

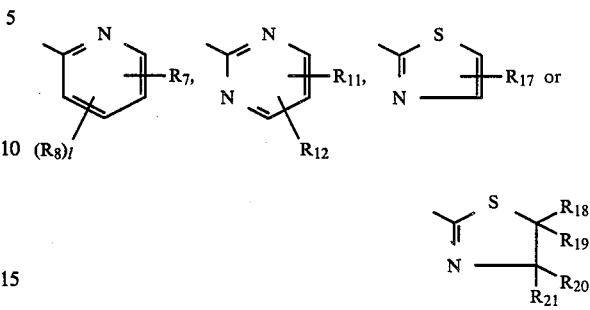

(in which $R_7$, $R_8$, $R_{11}$, $R_{12}$ and $R_{17}$ are each a hydrogen atom or a fluorine atom, $R_{18}$, $R_{19}$, $R_{20}$ and $R_{21}$ are each a hydrogen atom and l is as defined above;
$R_2$ and $R_3$ are, the same or different, each a hydrogen atom, a halogen atom or a methyl group;
$R_5$ and $R_6$ are, the same or different, each a hydrogen atom or a fluorine atom;
X is an oxygen atom or a sulfur atom;
Y is an oxygen atom;
Z is an oxygen atom or a methylene group; and
m and n are each an integer of 0.

The intermediates in the production of the nitrogen-containing heterocyclic compounds (I) are also included in the scope of this invention. Among a variety of intermediates, those of the following formula are particularly important:

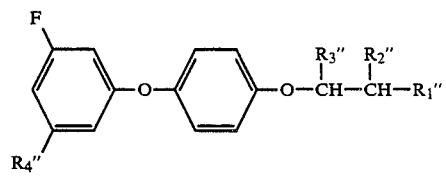

wherein $R_1''$ is a halogen atom, a hydroxyl group, a tosyloxy group or a mesyloxy group, $R_2''$ and $R_3''$ are, the same or different, each a hydrogen atom or a methyl group and $R_4''$ is a hydrogen atom or a fluorine atom.

Organophosphorus insecticides, organochlorinated insecticides, carbamate insecticides, etc. have made a great contribution to prevention and extermination of harmful insects. Some of these insecticides, however, exhibit a high toxicity. Further, their residual effect causes sometimes unfavorable abnormality in the ecosystem of insects. Furthermore, a resistance to the insecticides is noticed in house flies, planthoppers, leafhoppers, rice borers, etc.

In order to solve the above problems, an extensive study was carried out to provide an excellent insecticide which shows at a low concentration a high preventive effect attributable to a juvenile hormone-like activity; as a result, it has now been found that the nitrogen-containing heterocyclic compounds (I) of the invention are useful for the control of insects in agricultural fields, forest lands, granaries, stored products, sanitary facilities, etc.

As the insecticide having a juvenile hormone-like activity, there is known "methoprene" (U.S. Pat. Nos.

3,904,662 and 3,912,815). The insecticidal acvitity of this knownn substance is still not satisfactory.

The nitrogen-containing heterocyclic compounds (I) of the invention show a juvenile hormone-like controlling effect and therefore can be used in a low concentration for the control of a variety of insects belonging to Coleoptera, Lepidoptera, Hemiptera, Dictyoptera, Diptera, etc. as well as spider mites (Teranychidae) belonging to Acarina in agricultural fields, forest lands, granaries, stored products, sanitary facilities, etc.

The nitrogen-containing heterocyclic compounds (I) can be prepared by various procedures, of which typical examples are shown below.

Procedure A

A compound of the formula:

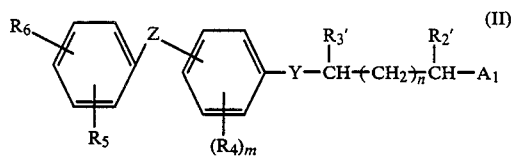

wherein $R_4$, $R_5$, $R_6$, Y, Z, m and n are each as defined above, $R_2'$ and $R_3'$ are, the same or different, each a hydrogen atom or a methyl group and $A_1$ is a halogen atom, a mesyloxy group or a tosyloxy group is reacted with a compound of the formula:

$$H-X-R_1 \quad (III)$$

wherein $R_1$ and X are each as defined above, or its alkali metal salt, to give the nitrogen-containing heterocyclic compound (I).

The reaction is usually carried out in the absence or presence of an inert solvent (e.g. dimethylformamide, dimethylsulfoxide, tetrahydrofuran, dimethoxyethane, toluene) in the existence of an acid accepting agent such as an alkali metal, an alkali metal hydride, an alkali metal amide, an alkali metal hydroxide, an alkali metal carbonate, an alkyl lithium or an organic base at a temperature of $-70°$ C. to the boiling temperature of the reaction mixture, preferably from room temperature to 110° C., for a period of 0.5 to 24 hours. In order to accelerate the reaction, a phase transfer catalyst such as benzyltriethylammonium chloride or tetra-n-butylammonium bromide may be employed. In this case, water is usable as the solvent.

The molar ratio of the compound (II) and the compound (III) is normally 1:1-10, preferably 1:1.1-1.5.

Procedure B

A compound of the formula:

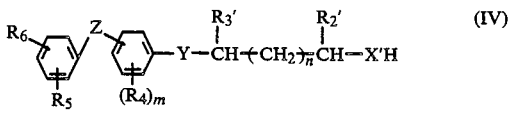

wherein $R_2'$, $R_3'$, $R_4$, $R_5$, $R_6$, Y, Z, m and n are each as defined above and X' is an oxygen atom or a sulfur atom or its alkali metal salt is reacted with a compound of the formula:

$$A_2-R_1 \quad (V)$$

wherein $R_1$ is as defined above and $A_2$ is a halogen atom to give the nitrogen-containing heterocyclic compound (I).

The reaction is usually carried out in the absence or presence of an inert solvent (e.g. dimethylformamide, dimethylsulfoxide, tetrahydrofuran, dimethoxyethane, toluene) in the existence of an acid accepting agent such as an alkali metal, an alkali metal hydride, an alkali metal amide, an alkali metal hydroxide, an alkali metal carbonate, an alkyl lithium or an organic base at a temperature of $-30°$ C. to the boiling temperature of the reaction mixture, preferably from room temperature to 110° C., for a period of 0.5 to 24 hours. In order to accelerate the reaction, a phase transfer catalyst such as benzyltriethylammonium chloride or tetra-n-butylammonium bromide may be employed. In this case, water is usable as the solvent.

The molar ratio of the compound (IV) and the compound (V) is normally 1:0.5-10, preferably 1:0.8-5.0.

Procedure C

The nitrogen-containing heterocyclic compounds (I) wherein $R_2$ or $R_3$ is a halogen atom can be prepared by reacting the corresponding non-halogenated compounds with a halogenating agent. For instance, the nitrogen-containing heterocyclic compound (I) wherein $R_1$ is

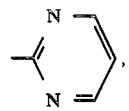

$R_2$ is chlorine, $R_3$, $R_5$ and $R_6$ are each hydrogen, X is sulfur, Y and Z are each oxygen and m and n are each 0, may be prepared by reacting a non-halogenated compound of the formula:

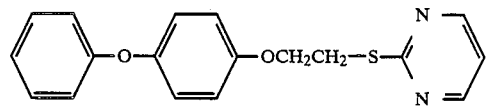

with an N-halosuccinimide of the formula:

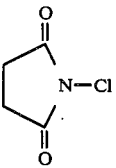

The above reaction may be carried out in an inert solvent (e.g. carbon tetrachloride, 1,2-dichloroethane, methylene chloride). If desired, a radical initiator such as α,α-azobisisobutylonitrile or benzoyl peroxide may be present in the reaction system so as to effect the reaction smoothly. No particular limitation is present on the reaction temperature but, in general, it may be performed at a temperature of 0° C. to the boiling temperature of the reaction mixture. The reaction is usually accomplished within a period of 1 to 50 hours. The halogenating agent such as N-halosuccinimide may be preferably used in an amount equimolar or more to the non-halogenated compound.

In the above procedures, the recovery of the produced nitrogen-containing heterocyclic compound (I)

from the reaction mixture and the purification of the recovered nitrogen-containing heterocyclic compound (I) may be carried out by per se conventional procedures. For instance, the purification can be achieved by recrystallization, chromatography, etc.

The nitrogen-containing heterocyclic compound (I) has optical isomers with respect to the groups $R_2$ and $R_3$, all of which are included within the scope of the invention. Further, the nitrogen-containing heterocyclic compounds (I) have a lone pair of electrons on nitrogen so that some of them can form salts with acids, and those salts are also included within the scope of the invention. Examples of the acid are inorganic acids (e.g. hydrochloric acid, hydrobromic acid, sulfuric acid), organic acids (e.g. trifluoroacetic acid, trichloroacetic acid), etc.

The compound (II) as one of the starting materials may be produced by per se conventional procedures, of which typical examples are shown in the following schema:

When Y is oxygen or sulfur:

(wherein $R_2'$, $R_3'$, $R_4$, $R_5$, $R_6$, Z, m and n are each as defined above, Y' is an oxygen atom or a sulfur atom and $W_1$ is an alkyl group).

Procedure (2)

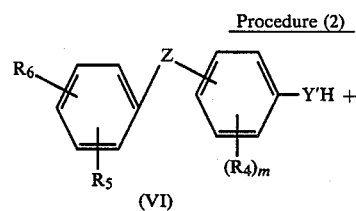

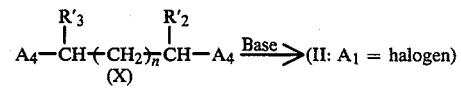

(wherein $R_2'$, $R_3'$, $R_4$, $R_5$, $R_6$, Y', Z, m and n are each as defined above and $A_4$ is a halogen atom).

Procedure (3)

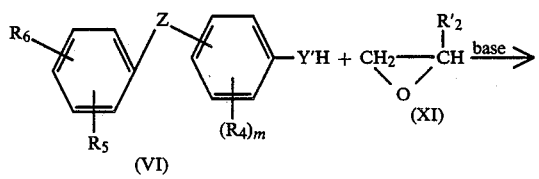

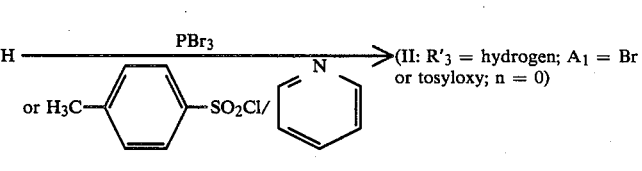

(wherein $R_2'$, $R_4$, $R_5$, $R_6$, Y', Z and m is as defined above).

Procedure (1)

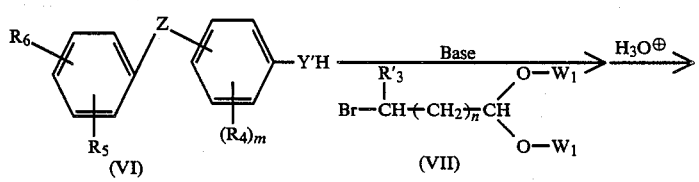

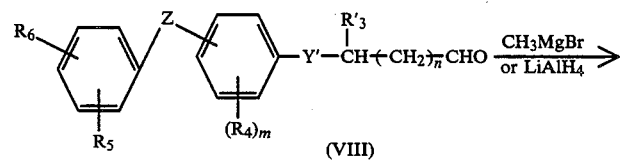

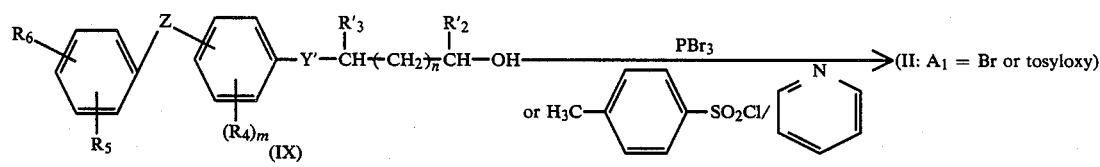

Procedure (4)

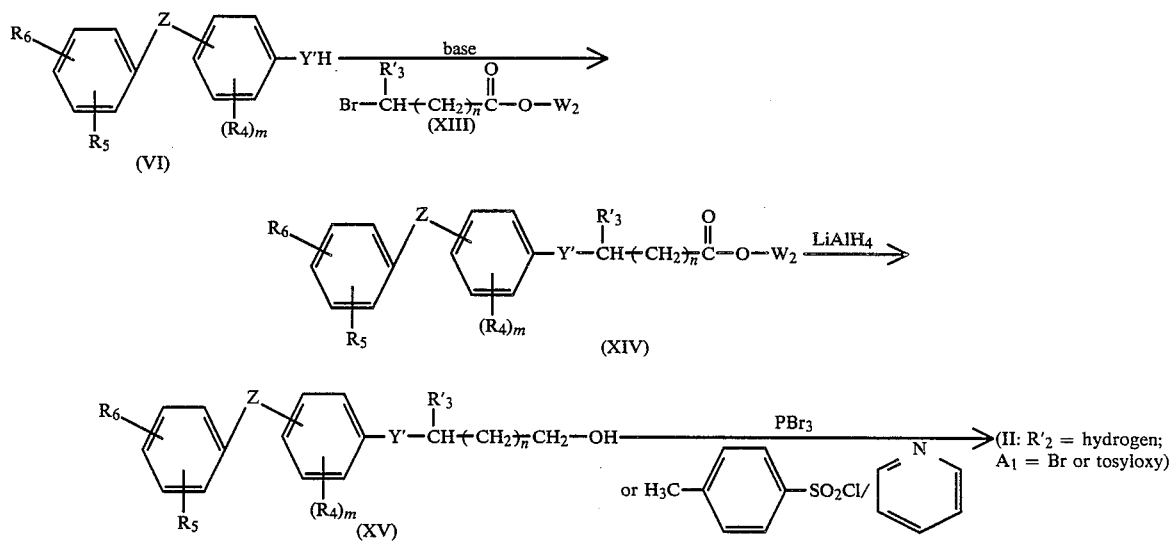

(wherein $R_3'$, $R_4$, $R_5$, $R_6$, $Y'$, $Z$, $m$ and $n$ are each as defined above and $W_2$ is an alkyl group).

When Y is methylene and n is zero:

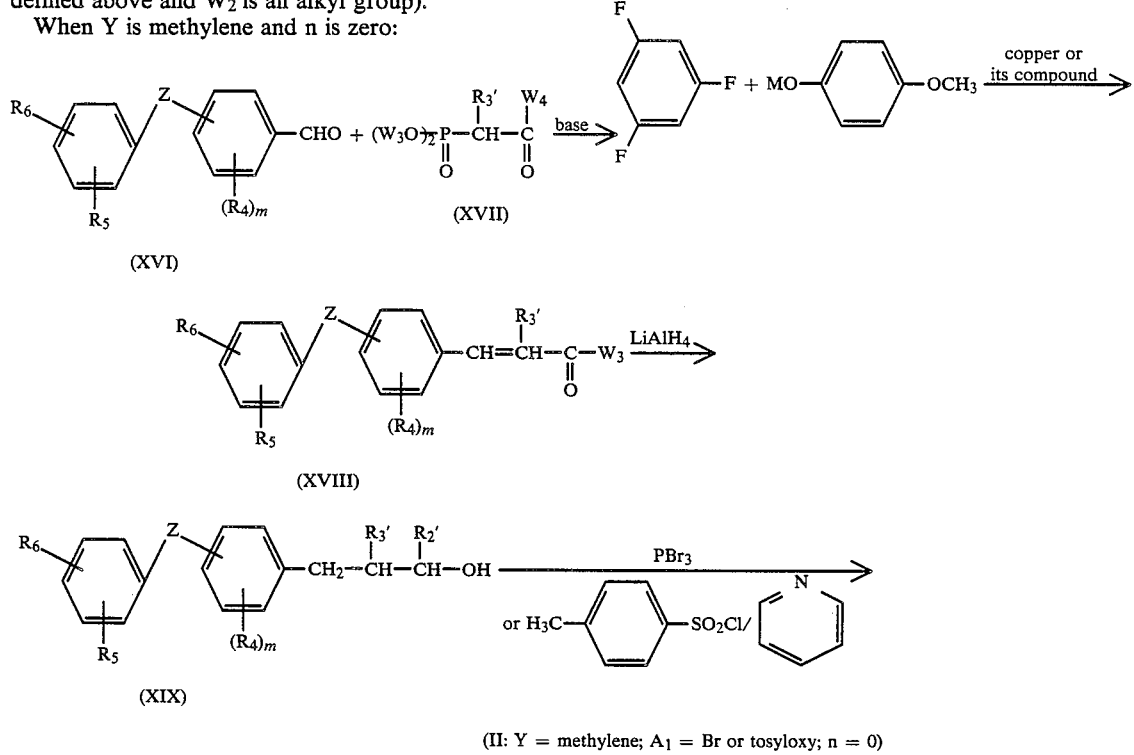

(wherein $R_2'$, $R_3'$, $R_4$, $R_5$, $R_6$, $Z$ and $m$ are each as defined above, $W_3$ is an alkyl group and $W_4$ is a methyl group or an alkoxy group).

The compound (VI) is known or can be prepared by per se conventional procedures (cf. Angew. Chem., 52, 915 (1938); Japanese patent publn. (unexamined) No. 62033/1980). A typical example for producing the compound (VI), e.g. 4-(3,5-difluorophenoxy)phenol, is illustrated below.

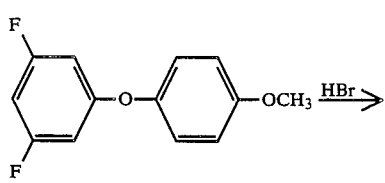

a sulfur atom may be produced in the following manner:

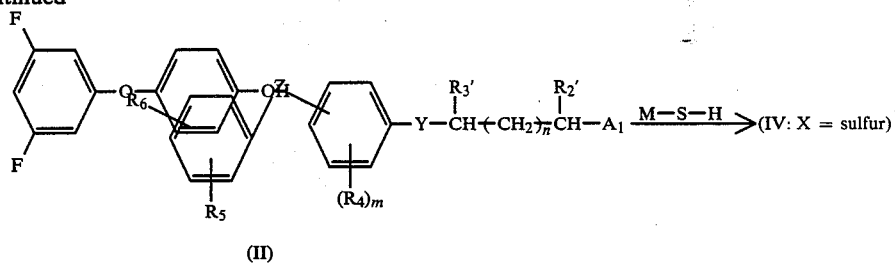

(wherein $R_2'$, $R_3'$, $R_4$, $R_5$, $R_6$, Y, Z, $A_1$, m and n are each as defined above and M is an alkali metal atom).

One of the optically active intermediary compounds of the invention, i.e. (S)-(+)-1-methyl-2-(4-phenoxyphenoxy)ethanol, is obtainable in the following manner:

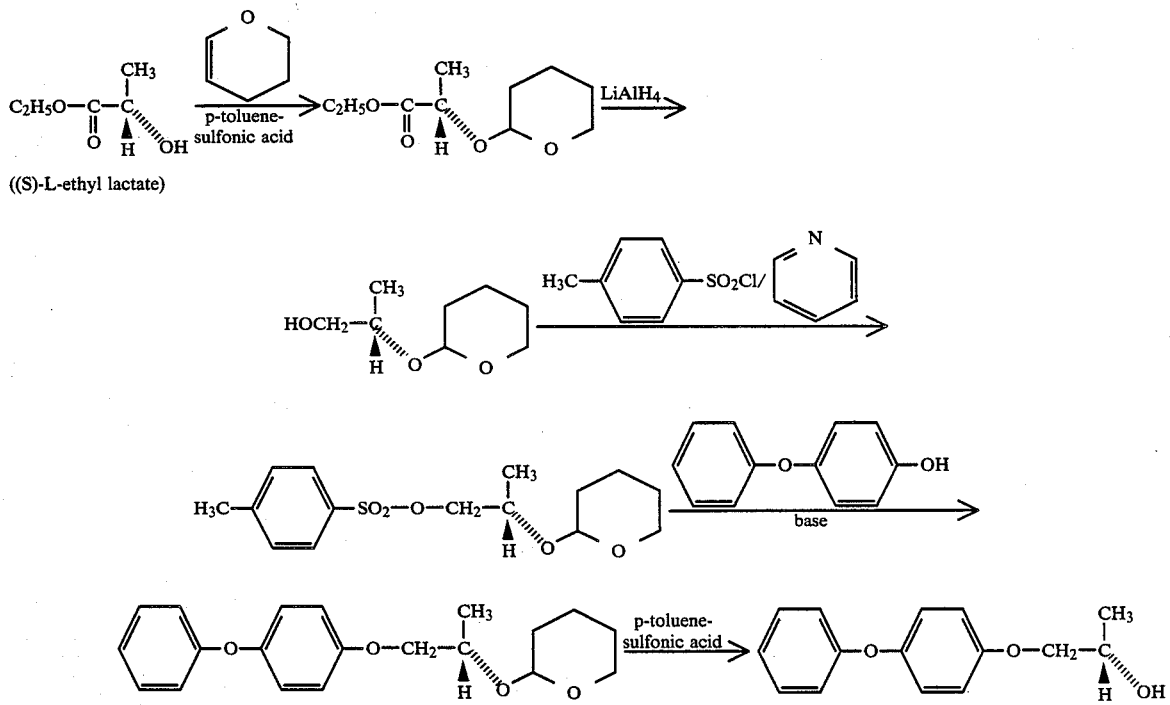

(wherein M is an alkali metal atom).

The compound (IV) wherein X is an oxygen atom is obtainable in the same similar manner as the preparation of the compound (II). The compound (IV) wherein X is Likewise, (R)-(−)-1-methyl-2-(4-phenoxyphenoxy)ethanol is prepared from (R)-D-ethyl lactate.

The (R)-(−)- or (S)-(+)-isomer of 1-methyl-2-(4-phenoxyphenoxy)ethanol can be converted into its corresponding another stereo-isomer according to the following steps:

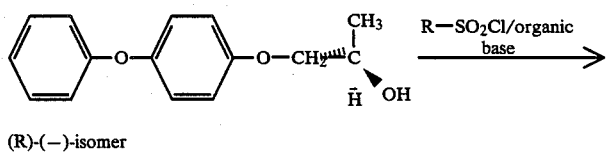

(R)-(−)-isomer

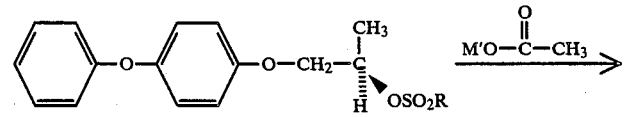

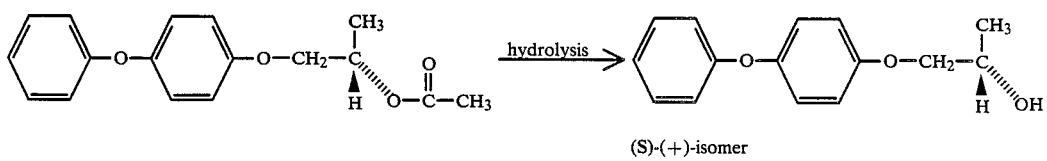

(S)-(+)-isomer wherein R is a p-tolyl group or a methyl group and M' is a sodium atom or a potassium atom.

Practical and presently preferred embodiments for preparation of the compound (I) are illustratively shown in the following Examples.

EXAMPLE 1

Preparation of Compound No. 1 (Procedure A):

To a suspension of sodium hydride (132 mg, 3.3 mmol; 60% in oil) in dimethylformamide (5 ml), a solution of 2-hydroxypyridine (314 mg, 3.3 mmol) in dimethylformamide (3 ml) was dropwise added with stirring, and stirring was continued at room temperature until the generation of hydrogen gas ceased. To the resultant solution, there was dropwise added a solution of 2-(4-phenoxyphenoxy)ethyl bromide (879 mg, 3.0 mmol) in dimethylformamide (3 ml), and the mixture was stirred at room temperature overnight. The reaction mixture was poured into water (70 ml) and extracted with toluene (25 ml) three times. The toluene layer was dried over anhydrous magnesium sulfate, and the solvent was removed by evaporation. The residue was purified by silica gel column chromatography to give 2-[2-(4-phenoxyphenoxy)ethoxy]pyridine (264 mg) as white crystals. M.P., 94.2° C.

EXAMPLE 2

Preparation of Compound No. 3 (Procedure B):

To a suspension of sodium hydride (200 mg, 5.0 mmol; 60% in oil) in dimethylformamide (5 ml), a solution of 1-methyl-2-(4-phenoxyphenoxy)ethanol (1.22 g, 5.0 mmol) in dimethylformamide (3 ml) was dropwise added with stirring, and the mixture was kept at an inner temperature of 50° to 60° C. until the generation of hydrogen gas ceased. 2-Chloropyridine (684 mg, 6.0 mmol) was dropwise added thereto, followed by stirring at 100° to 110° C. for 5 hours. The reaction mixture was cooled to room temperature, poured into water (100 ml) and extracted with toluene (40 ml) three times. The toluene layer was dried over anhydrous magnesium sulfate, and the solvent was removed by evaporation. The residue was purified by silica gel column chromatography to give 2-[1-methyl-2-(4-phenoxyphenoxy)ethoxy]pyridine (1.27 g) as pale yellow liquid. $n_D^{20.5}$ 1.5823. Upon being allowed to stand for a few days, the liquid solidified to give crystals. M.P., 49.7° C.

EXAMPLE 3

Preparation of Compound No. 12 (Procedure B):

To a suspension of sodium hydride (20 mg, 0.5 mmol; 60% in oil) in dimethylformamide (1 ml), a solution of 1-methyl-2-[4-(3,5-difluorophenoxy)phenoxy]ethanol (140 mg, 0.5 mmol) in dimethylformamide (1 ml) was dropwise added with stirring, and stirring was continued at room temperature until the generation of hydrogen gas ceased. 2-Fluoropyridine (97 mg, 1.0 mmol) was dropwise added thereto, and the mixture was stirred at room temperature overnight. The reaction mixture was poured into water (40 ml) and extracted with toluene (20 ml) three times. The toluene layer was dried over anhydrous magnesium sulfate, and the solvent was removed by evaporation. The residue was purified by silica gel column chromatography to give 2-{1-methyl-2-[4-(3,5-difluorophenoxy)phenoxy]ethoxy}pyridine (129 mg) as pale yellow liquid. $n_D^{19.0}$ 1.5602.

EXAMPLE 4

Preparation of Compound No. 49 (Procedure (A):

To a suspension of sodium hydride (160 mg, 4.0 mmol; 60% in oil) in dimethylformamide (5 ml), a solution of 2-mercapto-2-thiazoline (476 mg, 4.0 mmol) in dimethylformamide (3 ml) was dropwise added with stirring, and stirring was continued until the generation of hydrogen gas ceased. To the resultant solution, there was dropwise added a solution of 2-(4-phenoxyphenoxy)ethyl bromide (1.17 g, 4.0 mmol) in dimethylformamide (3 ml), and the mixture was stirred at room temperature overnight. The reaction mixture was poured into water (80 ml) and extracted with toluene (40 ml) three times. The toluene layer was dried over anhydrous magnesium sulfate, and the solvent was removed by evaporation. The residue was purified by silica gel column chromatography to give 2-[2-(4-phenoxyphenoxy)ethylthio]-2-thiazoline (887 mg) as pale yellow crystals. M.P., 88.6° C.

EXAMPLE 5

Preparation of Compound No. 20 (Procedure B):

(1) (S)-L-Ethyl lactate tetrahydropyranyl ether

L-Ethyl lactate (4.0 g, 34 mmol) and dihydropyrane (3.7 g, 44 mmol) were dissolved in dry diethyl ether (20 ml). To the resultant mixture, a solution of p-toluenesulfonic acid (50 mg) in dry ether (2 ml) was dropwise added at an inner temperature of 0° C., and the mixture was stirred at the same temperature for 2 hours and at 20° C. for 12 hours. The reaction mixture was poured into an ice-cooled 5% aqueous potassium carbonate solution and shaken. The ether layer was separated, washed with an aqueous sodium chloride solution and dried over anhydrous magnesium sulfate. Removal of ether gave almost pure (S)-L-ethyl lactate tetrahydropyranyl ether (6.6 g) as pale yellow liquid. $n_D^{22.0}$ 1.4395. $[\alpha]_D^{23} = -54.3°$(CHCl$_3$, c=0.56).

(2) (S)-2-(Tetrahydropyranyloxy)-1-propanol

To a solution of lithiumaluminum hydride (1.5 g, 40 mmol) in dry ether (50 ml), (S)-L-ethyl lactate tetrahydropyranyl ether obtained in (1) (6.6 g, 33 mmol) was dropwise added at an inner temperature of 0° to 10° C., and the mixture was stirred at the same temperature for 1 hour and at 20° C. for 1 hour. The reaction mixture was then poured into an ice-cooled aqueous ammonium chloride solution and extracted with ether. The ether layer was washed with an aqueous sodium chloride solution and dried over anhydrous magnesium sulfate. Removal of ether gave (S)-2-(tetrahydropyranyloxy)-propanol (4.2 g) as pale yellow liquid. $n_D^{22.5}$ 1.4552. $[\alpha]_D^{23} = -5.3°$(CHCl$_3$, c=0.51). IR (film: 3400, 2930, 1080, 1020 (strong).

(3) (S)-2-(Tetrahydropyranyloxy)-1-propyl p-toluenesulfonate p-Toluenesulfonyl chloride (5.5 g, 30 mmol) was added to a solution of (S)-2-(tetrahydropyranyloxy)-propanol as obtained (2) (4.2 g, 28 mmol) in pyridine (7 g) at a temperature of 0° to 5° C., and the resultant mixture was allowed to stand at 0° C. for 12 hours. The reaction mixture was poured into ice-water and extracted with ethyl acetate. The ethyl acetate layer was washed with water five times and then with an aqueous sodium chloride solution and dried over anhydrous magnesium sulfate. Removal of the solvent gave (S)-2-(tetrahydropyranyloxy)-1-propyl p-toluenesulfonate (6.8 g) as pale yellow liquid. $^1$H-NMR spectrum δ (CDCl$_3$, TMS): 1.13 (3H, m), 1.3–1.8 (6H), 2.39 (3H, s), 3.2–4.2 (5H), 4.52 (1H, broad m), 7.0–8.0 (4H).

(4) (S)-1-Methyl-2-(4-phenoxyphenoxy)ethanol

To a suspension of sodium hydride (0.84 g, 21 mmol; 60% in oil) in dimethylformamide (20 ml), 4-phenoxyphenol (4.20 g, 23 mmol) was gradually added under ice-cooling, and the mixture was stirred at 20° C. for 1 hour. (S)-2-(Tetrahydropyranyloxy)-1-propyl p-toluenesulfonate as obtained in (3) (6.39 g, 20 mmol) was added thereto, and the resultant mixture was stirred at an inner temperature of 70° C. for 7 hours. The reaction mixture was then poured into ice-water and extracted with ether twice. The ether layer was washed with a 3% aqueous sodium hydroxide solution so as to eliminate unreacted 4-phenoxyphenol. The ether layer was washed with an aqueous sodium chloride solution and dried over anhydrous magnesium sulfate. After removal of the solvent, methanol (50 ml) and p-toluenesulfonic acid (50 mg) were added to the residue, followed by stirring at 20° C. for 1 hour. The reaction mixture was poured into an aqueous sodium bicarbonate solution and extracted with ethyl acetate twice. The ethyl acetate layer was washed with an aqueous sodium chloride solution and dried over anhydrous magnesium sulfate. After removal of the solvent, the residue was purified by silica gel column chromatography to give (S)-1-methyl-2-(4-phenoxyphenoxy)ethanol (2.30 g) as white crystals. M.P., 73.6° C. $[\alpha]_D^{23} = +18.5°$(CHCl$_3$, c=1.0).

(5) (S)-2-[1-Methyl-2-(4-phenoxyphenoxy)ethoxy]-pyridine

To a suspension of sodium hydride (80 mg, 2.0 mmol; 60% in oil) in dmethylformaide (5 ml), (S)-1-methyl-2-(4-phenoxyphenoxy)ethanol as obtained in (4) (500 mg, 2.0 mmol) was added at an inner temperature of 0° C., and the resultant mixture was stirred at 0° C. for 30 minutes and at 20° C. for 1 hour. 2-Fluoropyridine (280 mg, 2.9 mmol) was added thereto, and stirring was continued at 20° C. for 12 hours. The reaction mixture was poured into ice-water and extracted with ethyl acetate twice. The ethyl acetate layer was washed with an aqueous sodium chloride solution and dried over anhydrous magnesium sulfate. After removal of the solvent, the residue was purified by silica gel column chromatography to give (S)-2-[1-methyl-2-(4-phenoxyphenoxy)ethoxy]pyridine (370 mg) as pale yellow liquid. $n_D^{23.0}$1.5828. $[\alpha]_D^{23} = -33.8°$(CHCl$_3$, c=0.34).

EXAMPLE 6

Preparation of Compound No. 118 (Procedure A):

To a solution of α-picoline (1.0 g, 11 mmol) in dry tetrahydrofuran (20 ml), n-butyl lithium (8 ml, 11 mmol; 1.4 mmol/ml) was added at −50° C. under nitrogen stream until the reaction mixture turned red. After stirring at −50° C. for 30 minutes, 2-(4-phenoxyphenoxy)ethyl bromide (3.0 g, 10 mmol) was dropwise added thereto at −50° C., and stirring was continued at the same temperature for 2 hours and at 20° C. for 12 hours. The reaction mixture was poured into ice-water and extracted with thyl acetate. The ethyl acetate layer was washed with an aqueous sodium chloride solution and dried over anhydrous magnesium sulfate. After removal of the solvent, the residue was purified by silica gel column chromatography to give 2-[3-(4-phenoxyphenoxy)propyl]pyridine (1.6 g) as pale yellow oil. $n_D^{24.5}$1.5861.

EXAMPLE 7

Preparation of Compound No. 111 (Procedure C):

To a solution of 2-[2-(4-phenoxyphenoxy)ethylthio]-pyrimidine (324 mg, 1.0 mmol) in carbon tetrachloride (3 ml), there was added N-chlorosuccinimide (160 mg, 1.2 mmol) with stirring under ice-cooling. The reaction system was gradually elevated to room temperature, and stirring was continued overnight. The precipitate was separated by filtration, and the filtrate was concentrated. Recrystallization of the residue from cyclohexane gave 2-[1-chloro-2-(4-phenoxyphenoxy)ethylthio]-pyrimidine (268 mg) as pale yellow crystals. M.P., 86.0° C.

EXAMPLE 8

Preparation of Compound No. 3 (Procedure B):

A mixture of 1-methyl-2-(4-phenoxyphenoxy)ethanol (2.0 g, 8.2 mmol), 2-chloropyridine (4.0 g, 35 mmol), flaked 95% sodium hydroxide (1 g, 24 mmol) and tetra-n-butylammonium bromide (0.13 g) was stirred at an inner temperature of 85° to 90° C. for 6 hours. After allowed to cool, toluene (10 g) was added thereto, and the resultant mixture was washed with water and extracted with 35% hydrochloric acid (5 g) twice. The hydrochloric acid layer was washed with toluene (10 g). A 10% aqueous sodium hydroxide solution was added thereto to make the mixture sufficiently basic. The basic mixture was further extracted with toluene (10 g) twice, and the toluene layer was washed with a 10% aqueous sodium hydroxide solution and a saturated aqueous sodium chloride solution in order and dried over anhydrous magnesium sulfate. After removal of the solvent, the residue was purified by silica gel column chromatography to give 2-[1-methyl-2-(4-phenoxyphenoxy)ethoxy]pyridine (1.87 g) as white crystals.

EXAMPLE 9

Preparation of Compound No. 3 (Procedure B):

To a mixture of sodium hydride (0.61 g, 15 mmol; 60% in oil) and 2-chloropyridine (1 g, 9 mmol), there was dropwise added a mixture of 1-methyl-2-(4-phenoxyphenoxy)ethanol (3.0 g, 12 mmol) and 2-chloropyridine (5 g, 44 mmol) with stirring at an inner temperature of 0° to 5° C. Tetra-n-butylammonium bromide (0.2 g) was added to the resultant mixture, and stirring was continued at room temperature for 40 minutes and at an inner temperature of 85° to 90° C. for 6 hours. After allowed to cool, toluene (10 g) was added thereto, and the resultant mixture was washed with water and extracted with 35% hydrochloric acid (7.5 g) twice. To the hydrochloric acid layer, a 10% aqueous sodium hydroxide solution was added to make basic, followed by extraction with toluene (10 g) twice. The toluene extract was washed with a 10% aqueous sodium hydroxide solution and a saturated aqueous sodium chloride solution in order and dried over anhydrous magnesium sulfate. Removal of the solvent gave 2-[1-methyl-2-(4-phenoxyphenoxy)wethoxy]pyridine (3.51 g) as pale brown crystals.

EXAMPLE 10

Preparation of Compound No. 55:

Excess of gaseous hydrogen chloride was gradually introduced into a solution of 2-[2-(4-phenoxyphenoxy)ethoxy]pyridine (1.54 mg, 5.0 mmol) in toluene (50 ml) with stirring. The produced white precipitate was collected by filtration, washed with toluene several times and dried to give 2-[2-(4-phenoxyphenoxy)ethoxy]pyridinium hydrochloride (1.65 g) as white crystals. M.P., 138.1° C.

REFERENCE EXAMPLE 1

Preparation of (S)-(+)-1-methyl-2-(4-phenoxyphenoxy)ethanol:

A solution of 4-phenoxyphenol (2.14 g, 11.5 mmol) in toluene (7 ml) was poured into an aqueous solution (3 ml) of sodium hydroxide (0.92 g, 23.0 mmol), and (S)-(−)-propylene oxide (1.0 g, 17.24 mmol; a reagent manufactured by Aldrich; $[\alpha]_D^{20} = -7.2°(CHCl_3, c=1))$ was added thereto while stirring. To the resultant mixture, tetra-n-butylammonium bromide (185 mg) was added, and the mixture was stirred at room temperature for 12 hours, followed by addition of (S)-(−)-propylene oxide (1 g). After stirring at room temperature for 6 hours, the reaction mixture was vigorously stirred with addition of water (20 ml) and toluene (20 ml). The toluene layer was separated and washed with a 20% aqueous sodium hydroxide solution and an aqueous sodium chloride solution in order and dried over magnesium sulfate. Removal of the solvent gave crude (S)-(+)-1-methyl-2-(4-phenoxyphenoxy)ethanol (2.35 g), which was further purified by silica gel column chromatography to give (S)-(+)-1-methyl-2-(4-phenoxyphenoxy)ethanol (1.97 g). $[\alpha]_D^{23} = +14.0°(CHCl_3, c=1)$. ee.; 72.9%.

REFERENCE EXAMPLE 2

Preparation of (S)-1-methyl-2-(4-phenoxyphenoxy)ethyl acetate through (R)-1-methyl-2-(4-phenoxyphenoxy)ethyl methanesulfonate:

A mixture of anhydrous sodium acetate (82 mg, 1.0 mmol), (R)-1-methyl-2-(4-phenoxyphenoxy)ethyl methanesulfonate (250 mg, 0.78 mmol; ee.: 99.4%) and dimethylformide (5 ml) was stirred at an inner temperature of 100° to 110° C. for 5 hours. After allowed to cool, ice-water was added thereto, and the reaction mixture was extracted with toluene three times. The toluene layer was dried over anhydrous magnesium sulfate. The solvent was removed, and the residue was purified by thin layer chromatography using silica gel to give (S)-(−)-1-methyl-2-(4-phenoxyphenoxy)ethyl acetate (158 mg). $[\alpha]_D^{23} = -30.6°$ (CHCl$_3$, c=1). ee.: 88.8%.

REFERENCE EXAMPLE 3

Preparation of 4-(3,5-difluorophenoxy)anisole:

Sodium hydride (7.56 g, 0.189 mol; 60% in oil) was washed with n-hexane to eliminate the oil, and N,N-dimethylformamide (100 ml) was added thereto to make a suspension. To the thus prepared suspension, 4-methoxyphenol (25.84 g, 0.208 mol) was gradually added with stirring, and stirring was continued until the generation of hydrogen gas ceased. 1,3,5-Trifluorobenzene (30.00 g, 0.227 mol) and cuprous chloride (0.50 g) were added thereto. The resultant mixture was heaated under reflux for 8 hours with stirring. After allowed to cool, the reaction mixture was poured into ice-water and extracted with toluene. The toluene layer was dried over anhydrous magnesium sulfate.

The solvent was removed, and the residual oil was distilled under reduced pressure to give 4-(3,5-difluorophenoxy)anisole (25.42 g). B.P., 98.5° C./0.2 mmHg.

REFERENCE EXAMPLE 4

Preparation of 4-(3,5-difluorophenoxy)phenol:

A mixture of 4-(3,5-difluorophenoxy)anisole (22.0 g, 0.093 mol), acetic acid (200 ml) and a 47% aqueous hydrogen bromide solution (200 ml) was heated with stirring under reflux for 8 hours. After allowed to cool, the reaction mixture was poured into ice-water and extracted with a mixture of ether and n-hexane (1:2). The organic layer was washed with water three times and dried over anhydrous magnesium sulfate. Removal of the solvent gave 4-(3,5-difluorophenoxy)phenol (20.27 g).

REFERENCE EXAMPLE 5

Preparation of 2-[4-(3,5-difluorophenoxy)phenoxy]ethanol:

4-(3,5-Difluorophenoxy)phenol (9.0 g, 40.5 mmol) was added to an ethanolic solution of sodium ethoxide prepared from ethanol (40 ml) and sodium (939 mg, 40.9 mmol). To the resultant solution, 2-chloroethanol (3.26 g, 40.5 mmol) was dropwise added with stirring under reflux. After completion of the addition, the resultant mixture was stirred under reflux for 4 hours. After allowed to cool, ethanol was removed, and the residual oil was dissolved in toluene. The toluene layer was washed with water once, a 20% aqueous potassium hydroxide solution two times and a saturated aqueous sodium chloride solution once in order and dried over anhydrous magnesium sulfate. Removal of the solvent gave 2-[4-(3,5-difluorophenoxy)phenoxy]ethanol (6.50 g).

REFERNECE EXAMPLE 6

Preparation of 1-methyl-2-[4-(3,5-difluorophenoxy)phenoxy]ethanol:

4-(3,5-Difluorophenoxy)phenol (3.0 g, 13.5 mmol) was added to an ethanolic solution of sodium ethoxide prepared from ethanol (15 ml) and sodium (313 mg, 13.6 mmol). To the resultant solution, 1-chloro-2-propanol (1.60 g, 16.9 mmol) was dropwise added with stirring under reflux. After completion of the addition, the resultant mixture was stirred under reflux for 5 hours. After allowed to cool, ethanol was removed, and the residual oil was dissolved in toluene. The toluene layer was washed with water once, a 20% aqueous potassium hydroxide solution two times and a saturated aqueous sodium chloride solution once in order and dried over anhydrous magnesium sulfate. Removal of the solvent gave 1-methyl-2-[4-(3,5-difluorophenoxy)phenoxy]ethanol (2.24 g).

REFERENCE EXAMPLE 7

Preparation of 2-methyl-2-[4-(3,5-difluorophenoxy)phenoxy]ethanol:

A mixture of 4-(3,5-difluorophenoxy)phenol (11.1 g, 50.0 mmol), ethyl 2-bromopropionate (9.96 g, 55.0 mmol), potassium carbonate (7.25 g, 52.5 mmol) and N,N-dimethylformamide (50 ml) was stirred at an inner temperature of 70° to 80° C. for 3 hours. After allowed to cool, the reaction mixture was poured into ice-water and extracted with toluene. The toluene layer was dried over anhydrous magnesium sulfate, and the solvent was removed to give ethyl 2-[4-(3,5-difluorophenoxy)phenoxy]propionate (15.6 g).

The thus obtained ethyl 2-[4-(3,5-difluorophenoxy)phenoxy]propionate (15.6 g) was dissovled in diethyl ether (10 ml). The resulting solution was dropwise added to a suspension of lithium aluminum hydride (1.38 g, 36.3 mmol) in diethyl ether (70 ml) with stirring at an inner temperature of −20° to −10° C. After completion of the addition, stirring was continued for 1 hour while keeping the inner temperature at 0° to 5° C. The reaction mixture was poured into a mixture of ice and hydrochloric acid and extracted with ether. The ether layer was dried over anhydrous magnesium sulfate, and the solvent was removed to give 2-methyl-2-[4-(3,5-difluorophenoxy)phenoxy]ethanol (12.6 g).

REFERENCE EXAMPLE 8

Preparation of 2-[4-(3,5-difluorophenoxy)phenoxy]ethyl bromide:

To a mixture of 2-[4-(3,5-difluorophenoxy)phenoxy]ethanol (1.00 g, 3.76 mmol) and n-hexane (50 ml), phosphorus tribromide (0.71 g, 2.63 mmol) was gradually added with stirring under ice-cooling. After completion of the addition, the temperature was elevated to room temperature and stirred was continued at the same temperature for 30 minutes, followed by stirring under reflux for 1 hour. After allowed to cool, the upper n-hexane layer was collected by decantation, and the n-hexane layer was washed with water two times, an aqueous sodium carbonate solution three times and a saturated aqueous sodium chloride solution once in order and dried over anhydrous magnesium sulfate. Removal of the solventgave 2-[4-(3,5-difluorophenoxy)phenoxy]ethyl bromide (915 mg).

REFERENCE EXAMPLE 9

Preparation of 2-[4-(3,5-difluorophenoxy)phenoxy]ethyl p-toluenesulfonate:

To a solution of 2-[4-(3,5-difluorophenoxy)phenoxy]ethanol (2.66 g, 10.0 mmol) in pyridine (2.8 g), p-toluenesulfonyl chloride (1.91 g, 10.0 mmol) was gradually added with stirring while cooling at −20° C., and the resultant mixture was allowed to stand in a refrigerator overnight. Diethyl ether was added to the reaction mixture, which was washed with dilute hydrochloric acid until the aqueous layer became acidic, followed by washing with an aqueous sodium bicarbonate solution and a saturated aqueous sodium chloride solution. The obtained ether layer was dried over anhydrous magnesium sulfate, and the solvent was removed to give 2-[4-(3,5-difluorophenoxy)phenoxy]ethyl p-toluenesulfonate (3.90 g).

In the same manner as above, there were prepared the nitrogen-containing heterocyclic compounds (I) and the intermediates thereto. Some typical examples of them are shown in Tables 1 to 3.

TABLE 1

$$R_3 \quad R_2$$
$$Y-CH-(CH_2)_n-CH-X-R_1$$

[phenyl ring with $(R_4)_m$, Z linking to second phenyl ring with $R_5$, $R_6$]

Position of
[phenyl with Z, $R_5$, $R_6$]

| Compound No. | $R_1$ | $R_2$ | $R_3$ | $R_4$ | $R_5$ | $R_6$ | Position of $R_5$ | X | Y | Z | m | n | Physical constant |
|---|---|---|---|---|---|---|---|---|---|---|---|---|---|
| 1 | pyridyl | H | H | H | H | H | 4- | O | O | O | 0 | 0 | M.P. 94.2° C. |
| 2 | pyridyl | H | H | H | H | H | 4- | S | O | O | 0 | 0 | M.P. 81.6° C. |
| 3 | pyridyl | CH$_3$ | H | H | H | H | 4- | O | O | O | 0 | 0 | $n_D^{20.5}$ 1.5823; M.P. 49.7° C. |
| 4 | pyridyl | H | CH$_3$ | H | H | H | 4- | O | O | O | 0 | 0 | $n_D^{21.0}$ 1.5775 |
| 5 | pyridyl | CH$_3$ | H | H | H | H | 4- | O | O | S | 0 | 0 | $n_D^{19.0}$ 1.5963 |
| 6 | pyridyl | CH$_3$ | H | H | 3-F | H | 4- | O | O | O | 0 | 0 | $n_D^{20.5}$ 1.5721 |

TABLE 1-continued
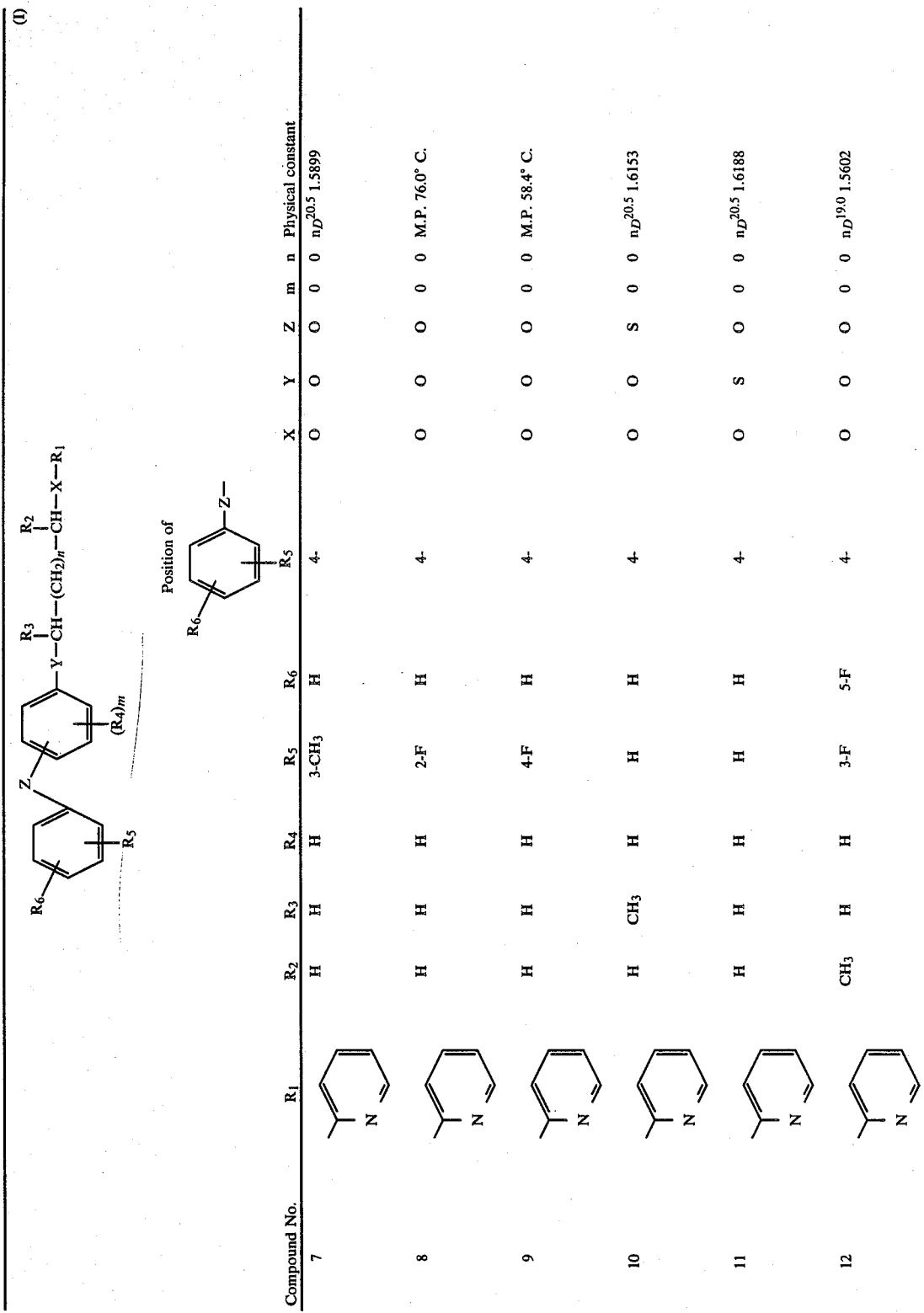
| Compound No. | $R_1$ | $R_2$ | $R_3$ | $R_4$ | $R_5$ | $R_6$ | Position of $R_5$ | X | Y | Z | m | n | Physical constant |
|---|---|---|---|---|---|---|---|---|---|---|---|---|---|
| 7 | 2-pyridyl | H | H | H | 3-CH$_3$ | H | 4- | O | O | O | 0 | 0 | $n_D^{20.5}$ 1.5899 |
| 8 | 2-pyridyl | H | H | H | 2-F | H | 4- | O | O | O | 0 | 0 | M.P. 76.0° C. |
| 9 | 2-pyridyl | H | H | H | 4-F | H | 4- | O | O | O | 0 | 0 | M.P. 58.4° C. |
| 10 | 2-pyridyl | H | CH$_3$ | H | H | H | 4- | O | O | O | 0 | 0 | $n_D^{20.5}$ 1.6153 |
| 11 | 2-pyridyl | H | H | H | H | H | 4- | O | S | S | 0 | 0 | $n_D^{20.5}$ 1.6188 |
| 12 | 2-pyridyl | CH$_3$ | H | H | 3-F | 5-F | 4- | O | O | O | 0 | 0 | $n_D^{19.0}$ 1.5602 |

TABLE 1-continued $$\begin{array}{c} R_2 \\ | \\ R_3-CH-(CH_2)_n-CH-X-R_1 \\ | \\ Y \end{array}$$ (I)

| Compound No. | R1 | R2 | R3 | R4 | R5 | R6 | Position of Z | X | Y | Z | m | n | Physical constant |
|---|---|---|---|---|---|---|---|---|---|---|---|---|---|
| 13 | pyridyl | CH3 | H | 2-CH3* | H | H | 4- | O | O | O | 1 | 0 | $n_D^{20.5}$ 1.5791 |
| 14 | pyridyl | H | CH3 | H | 3-OCHF2 | H | 4- | O | O | O | 0 | 0 | |
| 15 | pyridyl | CH3 | H | H | H | H | 4- | O | O | O | 0 | 0 | $n_D^{21.0}$ 1.5818 |
| 16 | pyridyl | H | H | H | H | H | 4- | O | O | CH2 | 0 | 0 | $n_D^{22.0}$ 1.5864 |
| 17 | pyridyl | CH3 | H | H | H | H | 4- | O | CH2 | O | 0 | 0 | $n_D^{21.5}$ 1.5781 |
| 18 | pyridyl | H | CH3 | H | H | H | 4- | O | CH2 | O | 0 | 0 | $n_D^{22.0}$ 1.5791 |

TABLE 1-continued $$\text{R}_6\underset{\text{R}_5}{\overset{\text{Z}}{\bigcirc}}\text{—Y—CH}(\text{R}_3)\text{—(CH}_2)_n\text{—CH}(\text{R}_2)\text{—X—R}_1 \quad (\text{R}_4)_m \tag{I}$$

Position of Z—⌬—R$_5$, R$_6$

| Compound No. | R$_1$ | R$_2$ | R$_3$ | R$_4$ | R$_5$ | R$_6$ | X | Y | Z | m | n | Physical constant |
|---|---|---|---|---|---|---|---|---|---|---|---|---|
| 19 | 4-phenoxyphenyl-O-CH(CH$_3$)- (pyridin-2-yloxy) | | | | | | | | | | | (R/S = 99.7/0.3) ((R)-isomer of Compound No. 3) [α]$_D^{23}$ = +39.4° (CHCl$_3$, c = 0.34) |
| 20 | 4-phenoxyphenyl-O-CH(CH$_3$)- (pyridin-2-yloxy) | | | | | | | | | | | (R/S = 1.8/98.2) ((S)-isomer of Compound No. 3) [α]$_D^{23}$ = −33.8° (CHCl$_3$, c = 0.34) |
| 21 | 3-pyridyl | H | H | H | H | H | O | O | O | 0 | 4 | M.P. 58.6° C. |
| 22 | 4-pyridyl | H | H | H | H | H | O | O | O | 0 | 4 | M.P. 121.9° C. |
| 23 | 2-pyridyl | H | H | H | 3-Cl | 5-Cl | O | O | O | 0 | 4 | M.P. 94.2° C. |

TABLE 1-continued $$R_3\text{—}Y\text{—}CH\text{—}(CH_2)_n\text{—}CH\text{—}X\text{—}R_1 \quad (I)$$

(with substituents $R_2$, $R_4$, $R_5$, $R_6$, $Z$ on phenyl rings)

| Compound No. | $R_1$ | $R_2$ | $R_3$ | $R_4$ | $R_5$ | $R_6$ | Position of phenyl-Z | X | Y | Z | m | n | Physical constant |
|---|---|---|---|---|---|---|---|---|---|---|---|---|---|
| 24 | 2-CH₃-pyridyl | H | H | H | H | H | 4- | O | O | O | 0 | 0 | M.P. 90.5° C. |
| 25 | 6-CH₃-pyridyl | H | H | H | H | H | 4- | O | O | O | 0 | 0 | M.p. 54.5° C. |
| 26 | 5-NO₂-pyridyl | H | H | H | H | H | 4- | O | O | O | 0 | 0 | M.p. 112.7° C. |
| 27 | 6-OCH₃-pyridyl | H | H | H | H | H | 4- | O | O | O | 0 | 0 | M.P. 63–65° C. |
| 28 | 6-Cl-pyridyl | H | H | H | H | H | 4- | O | O | O | 0 | 0 | M.P. 77–79° C. |

TABLE 1-continued
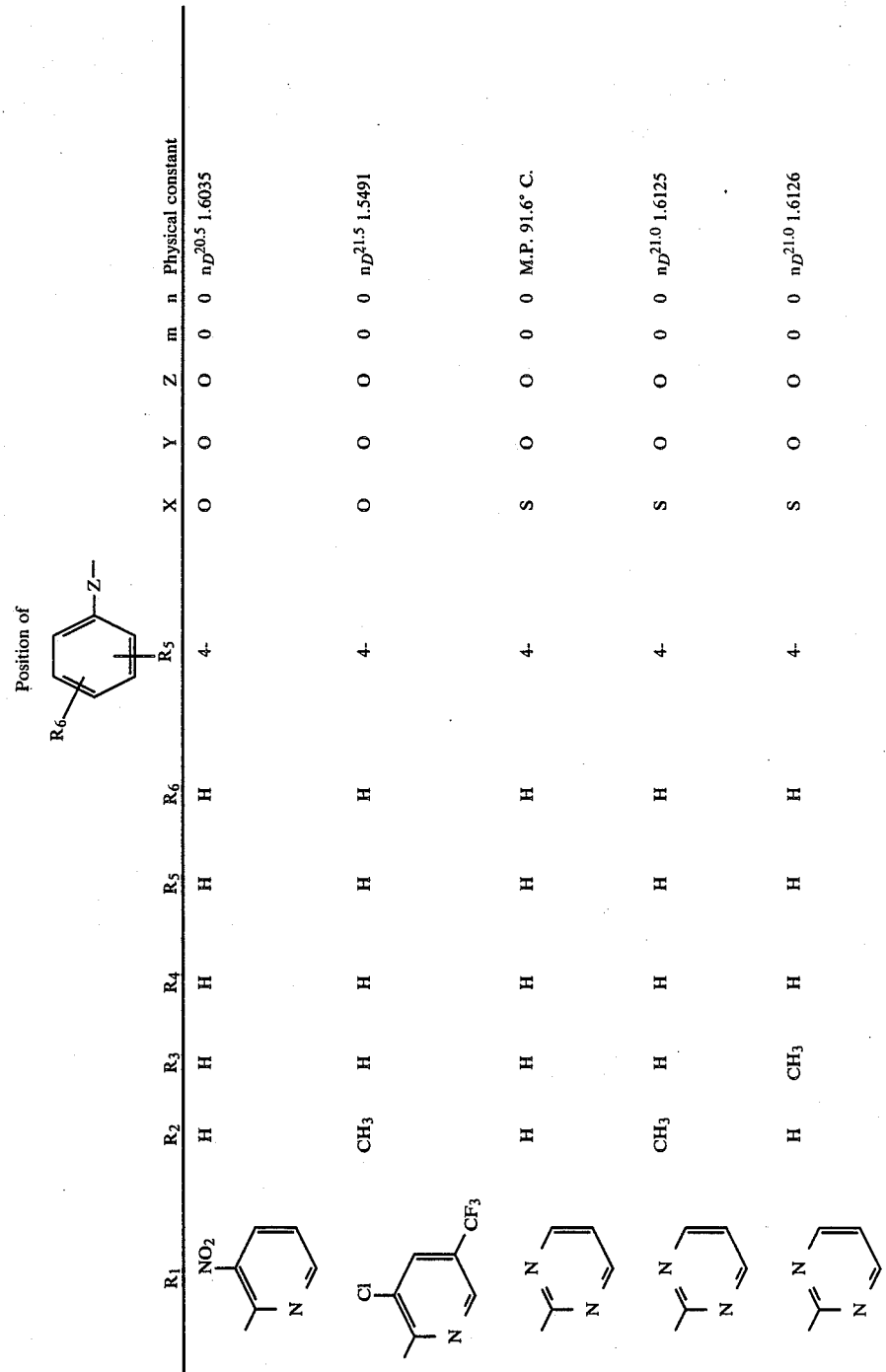
| Compound No. | R₁ | R₂ | R₃ | R₄ | R₅ | R₆ | Position of R₅ | X | Y | Z | m | n | Physical constant |
|---|---|---|---|---|---|---|---|---|---|---|---|---|---|
| 29 | 3-NO₂-2-pyridyl | H | H | H | H | H | 4- | O | O | O | 0 | 0 | $n_D^{20.5}$ 1.6035 |
| 30 | 3-Cl-5-CF₃-2-pyridyl | CH₃ | H | H | H | H | 4- | O | O | O | 0 | 0 | $n_D^{21.5}$ 1.5491 |
| 31 | 2-pyrimidyl | H | H | H | H | H | 4- | S | O | O | 0 | 0 | M.P. 91.6° C. |
| 32 | 2-pyrimidyl | CH₃ | H | H | H | H | 4- | S | O | O | 0 | 0 | $n_D^{21.0}$ 1.6125 |
| 33 | 2-pyrimidyl | H | CH₃ | H | H | H | 4- | S | O | O | 0 | 0 | $n_D^{21.0}$ 1.6126 |

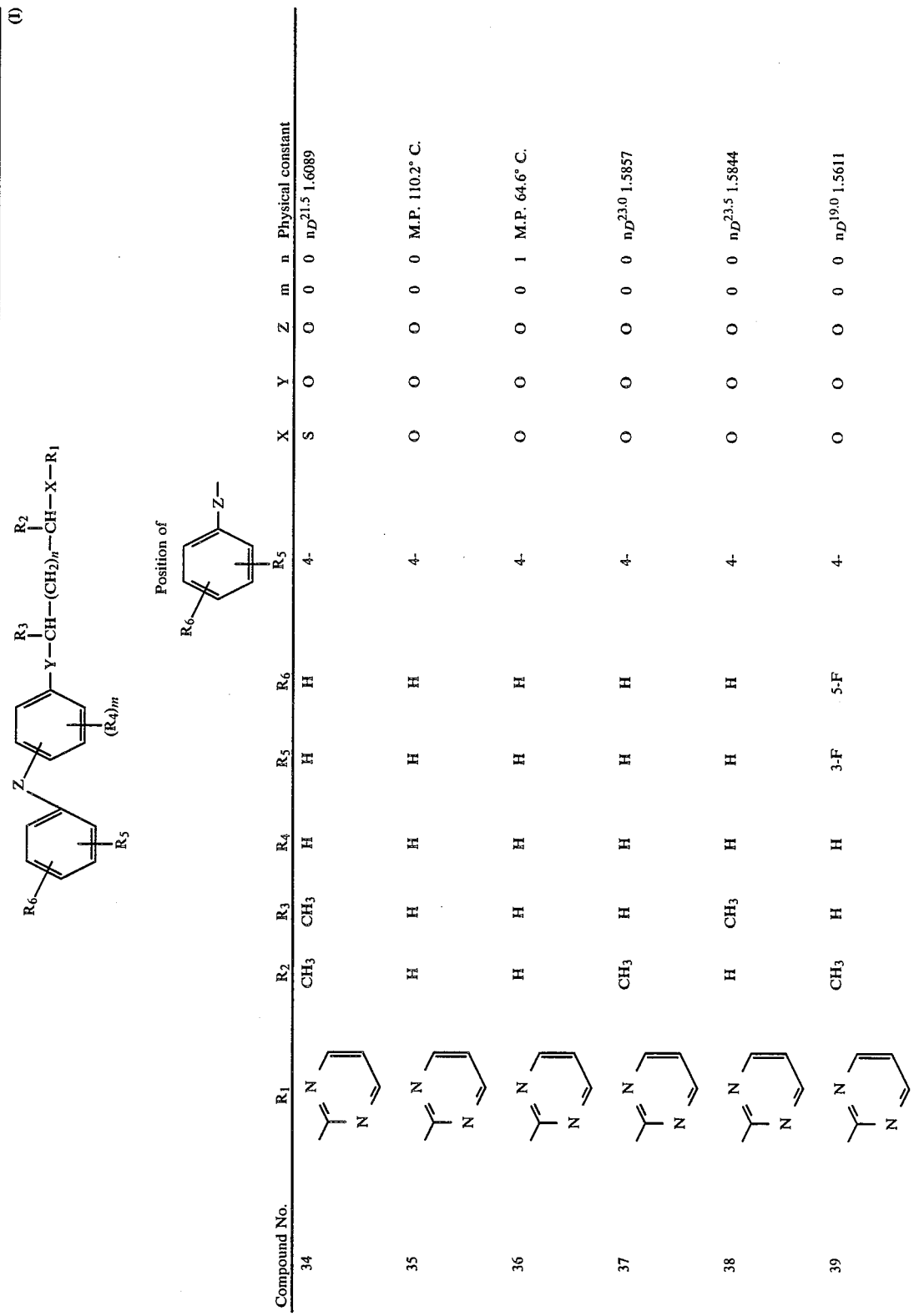
TABLE 1-continued
| Compound No. | R₁ | R₂ | R₃ | R₄ | R₅ | R₆ | Position of Z— | X | Y | Z | m | n | Physical constant |
|---|---|---|---|---|---|---|---|---|---|---|---|---|---|
| 34 | pyrimidinyl | CH₃ | CH₃ | H | H | H | 4- | S | O | O | 0 | 0 | $n_D^{21.5}$ 1.6089 |
| 35 | pyrimidinyl | H | H | H | H | H | 4- | O | O | O | 0 | 0 | M.P. 110.2° C. |
| 36 | pyrimidinyl | H | H | H | H | H | | O | O | O | 0 | 1 | M.P. 64.6° C. |
| 37 | pyrimidinyl | CH₃ | H | H | H | H | 4- | O | O | O | 0 | 0 | $n_D^{23.0}$ 1.5857 |
| 38 | pyrimidinyl | H | CH₃ | H | H | H | 4- | O | O | O | 0 | 0 | $n_D^{23.5}$ 1.5844 |
| 39 | pyrimidinyl | CH₃ | H | H | 3-F | 5-F | 4- | O | O | O | 0 | 0 | $n_D^{19.0}$ 1.5611 |

TABLE 1-continued (I) structure: Ar-Z-Ar'(R4)m-Y-CH(R3)-(CH2)n-CH(R2)-X-R1, with position of R5/R6 on phenyl-Z-

| Compound No. | R1 | R2 | R3 | R4 | R5 | R6 | Position of R5,R6 | X | Y | Z | m | n | Physical constant |
|---|---|---|---|---|---|---|---|---|---|---|---|---|---|
| 40 | 5-chloro-2-methylpyrimidin-4-yl | H | H | H | H | H | 4- | O | O | O | 0 | 0 | $n_D^{20.5}$ 1.5986 |
| 41 | 2-methyl-4-(methylthio)pyrimidin-5-yl (SCH3-pyrimidinyl) | H | H | H | H | H | 4- | O | O | O | 0 | 0 | M.P. 91.9° C. |
| 42 | 2,4,6-trimethylpyrimidin-5-yl | H | H | H | H | H | 4- | S | O | O | 0 | 0 | $n_D^{21.0}$ 1.6080 |
| 43 | 2,4,6-trimethylpyrimidin-5-yl | H | H | H | H | H | 4- | O | O | O | 0 | 0 | $n_D^{21.0}$ 1.5797 |
| 44 | 2-methylpyrimidin-5-yl | H | H | H | H | H | 4- | O | O | O | 0 | 0 | M.P. 91.3° C. |

TABLE 1-continued $$\text{R}_6 \underset{\text{R}_5}{\bigcirc}\!\!-\!Z\!-\!\underset{(R_4)_m}{\bigcirc}\!-\!Y\!-\!\overset{R_3}{\underset{|}{C}}\!H\!-\!(CH_2)_n\!-\!\overset{R_2}{\underset{|}{C}}\!H\!-\!X\!-\!R_1 \quad (I)$$

Position of $R_6\!\!-\!\!\bigcirc(R_5)\!\!-\!\!Z\!\!-$

| Compound No. | R₁ | R₂ | R₃ | R₄ | R₅ | R₆ | Position | X | Y | Z | m | n | Physical constant |
|---|---|---|---|---|---|---|---|---|---|---|---|---|---|
| 45 | 3-chloro-6-methylpyridazinyl | H | H | H | H | H | 4- | O | O | O | 0 | 0 | M.P. 124.1° C. |
| 46 | thiazolyl | H | H | H | H | H | 4- | O | O | O | 0 | 0 | M.P. 65.9° C. |
| 47 | thiazolyl | CH₃ | H | H | H | H | 4- | O | O | O | 0 | 0 | $n_D^{22.0}$ 1.5890 |
| 48 | nitrothiazolyl | H | H | H | H | H | 4- | O | O | O | 0 | 0 | $n_D^{22.5}$ 1.6031 |
| 49 | thiazolyl | H | H | H | H | H | 4- | S | O | O | 0 | 0 | M.P. 88.6° C. |
| 50 | thiazolyl | CH₃ | H | H | H | H | 4- | S | O | O | 0 | 0 | $n_D^{23.0}$ 1.6132 |
| 51 | thiazolyl | H | CH₃ | H | H | H | 4- | S | O | O | 0 | 0 | $n_D^{21.0}$ 1.6138 |

TABLE 1-continued
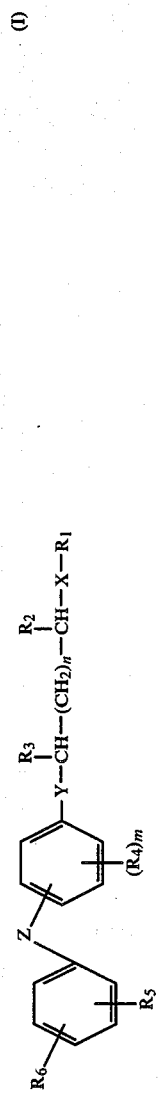
| Compound No. | R₁ | R₂ | R₃ | R₄ | R₅ | R₆ | Position of 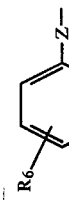 | X | Y | Z | m | n | Physical constant |
|---|---|---|---|---|---|---|---|---|---|---|---|---|---|
| 52 | 2-n) | H | H | H | H | H | 4 | S | O | O | 0 | 0 | M.P. 95.2° C. |
| 53 | -n) | H | H | H | H | H | 4 | S | O | O | 0 | 0 | $n_D^{23.5}$ 1.6117 |
| 54 | -ch2-n) | H | H | H | H | H | 4 | S | O | O | 0 | 0 | $n_D^{22.5}$ 1.6110 |
| 55 | HCl(hydrochloride of Compound No. 1) | | | | | | | | | | | | M.P. 138.1° C. |
| 56 | ![](s-c-n ring) | H | H | H | H | H | 4 | S | O | O | 0 | 0 | M.P. 96.4° C. |

TABLE 1-continued $$\text{R}_6\text{-}\underset{\text{R}_5}{\text{C}_6\text{H}_3}\text{-}\overset{Z}{N}\text{-}Y\text{-}\overset{R_3}{\underset{}{\text{CH}}}\text{-}(CH_2)_n\text{-}\overset{R_2}{\underset{}{\text{CH}}}\text{-}X\text{-}R_1 \quad (I)$$

$$(R_4)_m$$

Position of $R_6\text{-}\underset{R_5}{\text{C}_6\text{H}_3}\text{-}N\text{-}Z$

| Compound No. | R₁ | R₂ | R₃ | R₄ | R₅ | R₆ | Position | X | Y | Z | m | n | Physical constant |
|---|---|---|---|---|---|---|---|---|---|---|---|---|---|
| 57 | 2-pyridyl | H | CH₃ | H | 3-CF₃ | H | 4- | O | O | O | 0 | 0 | $n_D^{23.0}$ 1.5349 |
| 58 | 2-pyridyl | CH₃ | H | H | 3-OCH₃ | H | 4- | O | O | O | 0 | 0 | $n_D^{22.5}$ 1.5794 |
| 59 | 2,6-bis(SCH₃)pyrimidin-4-yl | CH₃ | H | H | H | H | 4- | O | O | O | 0 | 0 | $n_D^{23.0}$ 1.6114 |
| 60 | | | | | | | | | | | | | viscous liquid |
| 61 | 2-pyridyl | H | H | H | 3-F | H | 4- | O | O | O | 0 | 0 | M.P. 79.3° C. |

Compound 60: .HCl (hydrochloride of Compound No. 3)

TABLE 1-continued
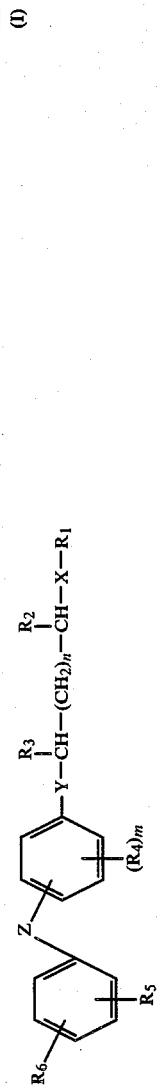
| Compound No. | R₁ | R₂ | R₃ | R₄ | R₅ | R₆ | Position of R₅ | X | Y | Z | m | n | Physical constant |
|---|---|---|---|---|---|---|---|---|---|---|---|---|---|
| 62 | pyridyl | H | H | H | 3-F | 5-F | 4- | O | O | O | 0 | 0 | M.P. 80.6° C. |
| 63 | pyrimidyl | H | H | H | 3-F | H | 4- | O | O | O | 0 | 0 | M.P. 92.8° C. |
| 64 | pyrimidyl | CH₃ | H | H | 3-F | H | 4- | O | O | O | 0 | 0 | $n_D^{28.5}$ 1.5660 |
| 65 | pyrimidyl | H | H | H | 3-F | H | 4- | O | O | O | 0 | 0 | M.P. 91.2° C. |
| 66 | thiazolyl | H | H | H | 3-F | 5-F | 4- | O | O | O | 0 | 0 | M.P. 71.7° C. |
| 67 | thiazolyl | CH₃ | H | H | 3-F | H | 4- | O | O | O | 0 | 0 | $n_D^{28.5}$ 1.5720 |

TABLE 1-continued $$\begin{array}{c} R_3 \\ | \\ Y-CH-(CH_2)_n-CH-X-R_1 \\ | \\ R_2 \end{array}$$ (I)

| Compound No. | R₁ | R₂ | R₃ | R₄ | R₅ | R₆ | Position of R₅ R₆ | X | Y | Z | m | n | Physical constant |
|---|---|---|---|---|---|---|---|---|---|---|---|---|---|
| 68 | (thiazolyl) | H | H | H | 3-F | 5-F | 4- | O | O | O | 0 | 0 | M.P. 74.2° C. |
| 69 | (thiazolyl) | CH₃ | H | H | 3-F | 5-F | 4- | O | O | O | 0 | 0 | $n_D^{29.0}$ 1.5599 |
| 70 | (tetrafluoropyridyl) | H | H | H | H | H | 4- | O | O | O | 0 | 0 | M.P. 80.9° C. |
| 71 | (fluoropyridyl) | H | H | H | H | H | 4- | O | O | O | 0 | 0 | M.P. 68.0° C. |
| 72 | (fluoropyridyl) | CH₃ | H | H | H | H | 4- | O | O | O | 0 | 0 | $n_D^{28.0}$ 1.5678 |

TABLE 1-continued
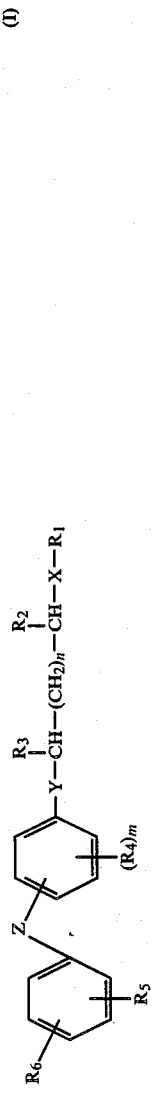
| Compound No. | R₁ | R₂ | R₃ | R₄ | R₅ | R₆ | Position of R₅ R₆ | X | Y | Z | m | n | Physical constant |
|---|---|---|---|---|---|---|---|---|---|---|---|---|---|
| 73 | 2-pyridyl | H | CH₃ | H | 3-F | 5-F | 4- | O | O | O | 0 | 0 | $n_D^{25.0}$ 1.5568 |
| 74 | 2-pyridyl | H | CH₃ | H | 3-F | H | 4- | O | O | O | 0 | 0 | $n_D^{25.0}$ 1.5686 |
| 75 | 2-pyrimidinyl | H | CH₃ | H | 3-F | H | 4- | O | O | O | 0 | 0 | $n_D^{25.0}$ 1.5705 |
| 76 | 2-pyrimidinyl | H | CH₃ | H | 3-F | 5-F | 4- | O | O | O | 0 | 0 | $n_D^{26.0}$ 1.5584 |
| 77 | 2-thiazolyl | H | CH₃ | H | H | H | 4- | O | O | O | 0 | 0 | $n_D^{24.5}$ 1.5864 |
| 78 | 2-thiazolyl | H | CH₃ | H | 3-F | H | 4- | O | O | O | 0 | 0 | $n_D^{24.5}$ 1.5737 |

TABLE 1-continued $$\text{(I)}$$

Structure:

$$\begin{array}{c} R_2 \\ | \\ \text{Ar}-\text{Y}-\text{CH}-(\text{CH}_2)_n-\text{CH}-\text{X}-R_1 \\ | \\ R_3 \end{array}$$

where Ar is a phenyl bearing $(R_4)_m$, $R_5$, $R_6$ and linked via N to another phenyl bearing Z.

| Compound No. | $R_1$ | $R_2$ | $R_3$ | $R_4$ | $R_5$ | $R_6$ | Position of $R_5$ | X | Y | Z | m | n | Physical constant |
|---|---|---|---|---|---|---|---|---|---|---|---|---|---|
| 79 | thiazolyl | H | CH$_3$ | H | 3-F | 5-F | 4- | O | O | O | 0 | 0 | M.P. 75.0° C. |
| 80 | thiazolyl | H | H | H | 3-F | 5-F | 4- | S | O | O | 0 | 0 | $n_D^{24.0}$ 1.5953 |
| 81 | thiazolyl | H | H | H | 3-F | H | 4- | S | O | O | 0 | 0 | $n_D^{24.0}$ 1.6103 |
| 82 | pyridyl | H | H | H | 3-F | 5-F | 4- | S | O | O | 0 | 0 | $n_D^{23.0}$ 1.5954 |
| 83 | pyridyl | H | H | H | 3-F | H | 4- | S | O | O | 0 | 0 | $n_D^{24.0}$ 1.6062 |
| 84 | pyrimidyl | H | H | H | 3-F | 5-F | 4- | S | O | O | 0 | 0 | $n_D^{23.5}$ 1.5950 |

TABLE 1-continued
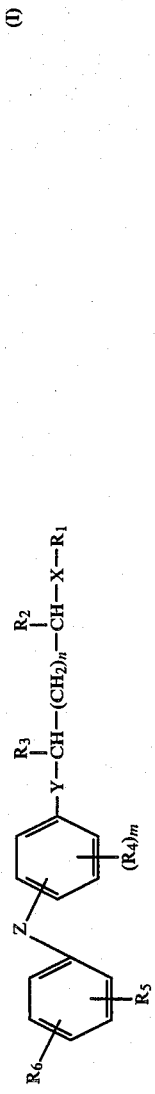
| Compound No. | R₁ | R₂ | R₃ | R₄ | R₅ | R₆ | Position of R₅ | X | Y | Z | m | n | Physical constant |
|---|---|---|---|---|---|---|---|---|---|---|---|---|---|
| 85 | (pyrimidinyl) | H | H | H | 3-F | H | 4 | S | O | O | 0 | 0 | $n_D^{24.0}$ 1.6085 |
| 86 | (thiazolinyl) | H | CH₃ | H | 3-F | 5-F | 4 | S | O | O | 0 | 0 | $n_D^{23.5}$ 1.5859 |
| 87 | (pyridyl) | H | CH₃ | H | 3-F | 5-F | 4 | S | O | O | 0 | 0 | $n_D^{23.5}$ 1.5864 |
| 88 | (pyrimidinyl) | H | CH₃ | H | 3-F | 5-F | 4 | S | O | O | 0 | 0 | $n_D^{23.0}$ 1.5858 |
| 89 | (6-Cl-pyridyl) | H | H | H | H | H | 4 | O | O | O | 0 | 0 | M.P. 74.5° C. |

TABLE 1-continued $$\text{structure (I): } R_5,R_6\text{-phenyl-Z-phenyl}(R_4)_m\text{-Y-CH}(R_3)-(CH_2)_n-CH(R_2)-X-R_1$$

| Compound No. | R₁ | R₂ | R₃ | R₄ | R₅ | R₆ | Position of R₅,R₆-phenyl | X | Y | Z | m | n | Physical constant |
|---|---|---|---|---|---|---|---|---|---|---|---|---|---|
| 90 | 2-Cl-6-methylpyridin-3-yl | CH₃ | H | H | H | H | 4- | O | O | O | 0 | 0 | $n_D^{23.5}$ 1.5865 |
| 91 | 3-Cl-2-methylpyridin-... | H | H | H | H | H | 4- | O | O | O | 0 | 0 | $n_D^{24.0}$ 1.5959 |
| 92 | 3-Cl-2-methylpyridin-... | CH₃ | H | H | H | H | 4- | O | O | O | 0 | 0 | $n_D^{24.5}$ 1.5735 |
| 93 | thiazolinyl | CH₃ | H | H | 3-F | 5-F | 4- | S | O | O | 0 | 0 | $n_D^{24.5}$ 1.5859 |
| 94 | 6-methylpyridin-2-yl | CH₃ | H | H | 3-F | 5-F | 4- | S | O | O | 0 | 0 | $n_D^{24.5}$ 1.5838 |

TABLE 1-continued
$$\text{(I)}$$
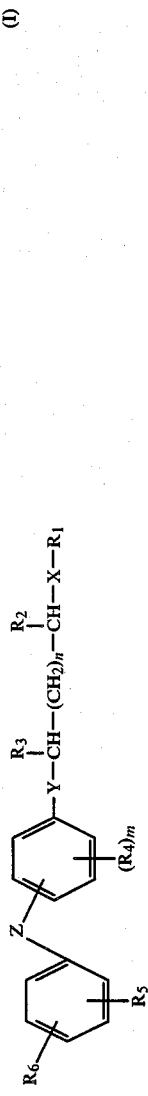
| Compound No. | R₁ | R₂ | R₃ | R₄ | R₅ | R₆ | Position of R₅ | X | Y | Z | m | n | Physical constant |
|---|---|---|---|---|---|---|---|---|---|---|---|---|---|
| 95 | (pyrimidine, 2-methyl) | CH₃ | H | H | 3-F | 5-F | 4- | S | O | O | 0 | 0 | $n_D^{24.5}$ 1.5850 |
| 96 | (6-chloro-2-pyridyl) | H | CH₃ | H | H | H | 4- | O | O | O | 0 | 0 | $n_D^{24.5}$ 1.5851 |
| 97 | (6-fluoro-2-pyridyl) | H | CH₃ | H | H | H | 4- | O | O | O | 0 | 0 | $n_D^{24.5}$ 1.5698 |
| 98 | (6-fluoro-2-pyridyl) | H | H | H | 3-F | H | 4- | O | O | O | 0 | 0 | M.P. 65.2° C. |
| 99 | (6-fluoro-2-pyridyl) | H | H | H | 3-F | 5-F | 4- | O | O | O | 0 | 0 | M.P. 87.4° C. |

TABLE 1-continued
$$\begin{array}{c} R_2 \\ | \\ Y-CH-(CH_2)_n-CH-X-R_1 \\ | \\ R_3 \end{array}$$ (I)
Position of 
| Compound No. | R₁ | R₂ | R₃ | R₄ | R₅ | R₆ | Position of Z— | X | Y | Z | m | n | Physical constant |
|---|---|---|---|---|---|---|---|---|---|---|---|---|---|
| 100 |  | H | CH₃ | H | 3-F | H | 4- | O | O | O | 0 | 0 | $n_D^{25.0}$ 1.5580 |
| 101 |  | H | CH₃ | H | 3-F | 5-F | 4- | O | O | O | 0 | 0 | $n_D^{25.0}$ 1.5468 |
| 102 |  | CH₃ | H | H | 3-F | H | 4- | O | O | O | 0 | 0 | $n_D^{25.0}$ 1.5601 |
| 103 |  | CH₃ | H | H | 3-F | 5-F | 4- | O | O | O | 0 | 0 | $n_D^{25.0}$ 1.5484 |
| 104 | (thiazoline) | H | CH₃ | H | 3-F | H | 4- | S | O | O | 0 | 0 | $n_D^{24.0}$ 1.5974 |

TABLE 1-continued $$\begin{array}{c} R_2 \\ | \\ \phantom{x}\text{—Y—CH—(CH}_2)_n\text{—CH—X—R}_1 \\ | \\ R_3 \end{array} \qquad (I)$$

Position of

| Compound No. | R₁ | R₂ | R₃ | R₄ | R₅ | R₆ | Position of R₅ | X | Y | Z | m | n | Physical constant |
|---|---|---|---|---|---|---|---|---|---|---|---|---|---|
| 105 | (2-pyridyl) | H | CH₃ | H | 3-F | H | 4- | S | O | O | 0 | 0 | $n_D^{24.0}$ 1.5961 |
| 106 | (2-pyrimidinyl) | H | CH₃ | H | 3-F | H | 4- | S | O | O | 0 | 0 | $n_D^{24.0}$ 1.5971 |
| 107 | (2-thiazolyl) | CH₃ | H | H | 3-F | H | 4- | S | O | O | 0 | 0 | $n_D^{24.0}$ 1.5990 |
| 108 | (2-pyridyl) | CH₃ | H | H | 3-F | H | 4- | S | O | O | 0 | 0 | $n_D^{24.0}$ 1.5960 |
| 109 | (2-pyrimidinyl) | CH₃ | H | H | 3-F | H | 4- | S | O | O | 0 | 0 | $n_D^{24.0}$ 1.5979 |
| 110 | (2-pyridyl) | CH₃ | H | 3-F* | H | H | 4- | O | O | O | 0 | 1 | 0 |

TABLE 1-continued
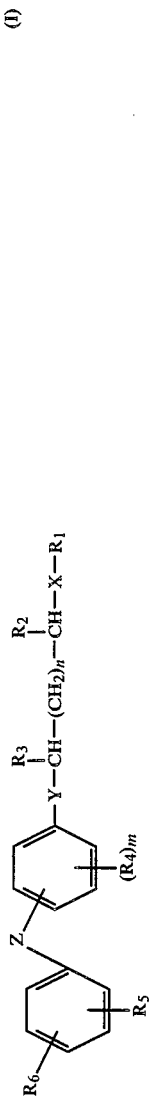
| Compound No. | R₁ | R₂ | R₃ | R₄ | R₅ | R₆ | R₄ | R₅ | R₆ | Position of 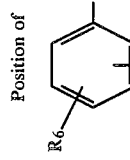 | X | Y | Z | m | n | Physical constant |
|---|---|---|---|---|---|---|---|---|---|---|---|---|---|---|---|---|
| 111 | (pyrimidinyl) | Cl | H | H | H | H | H | H | 4- | | S | O | O | 0 | 0 | M.P. 86.0° C. |
| 112 | (dichloropyrimidinyl) | H | H | H | H | H | H | H | 4- | | O | O | O | 0 | 0 | $n_D^{24.0}$ 1.5971 |
| 113 | (chloropyrimidinyl) | H | H | H | H | H | H | H | 4- | | O | O | O | 0 | 0 | M.P. 58.9° C. |
| 114 | (chloropyridazinyl) | H | H | H | H | H | H | H | 4- | | O | O | O | 0 | 0 | M.P. 79.9° C. |
| 115 | a mixture of | | | | | | | | | | | | | | | |

TABLE 1-continued $$Y-CH(R_3)-(CH_2)_n-CH(R_2)-X-R_1 \quad (I)$$

Position of R5 on the Z-linked phenyl ring

| Compound No. | R1 | R2 | R3 | R4 | R5 | R6 | Position of R5 | X | Y | Z | m | n | Physical constant |
|---|---|---|---|---|---|---|---|---|---|---|---|---|---|
| | 4,6-dichloropyrimidin-2-yl and 4,6-dichloro-2-methylpyrimidinyl isomers | H | H | H | H | H | 4 | O | O | O | 0 | 0 | $n_D^{22.5}$ 1.6037 |
| 116 | 2-pyridyl | CH3 | H | H | 2-F | H | 4 | O | O | O | 0 | 0 | $n_D^{22.5}$ 1.5723 |
| 117 | 2-pyridyl | CH3 | H | H | 4-F | H | 4 | O | O | O | 0 | 0 | $n_D^{22.5}$ 1.5705 |
| 118 | 2-pyridyl | H | H | H | H | H | 4 | CH2 | O | O | 0 | 0 | $n_D^{24.5}$ 1.5861 |

TABLE 1-continued $$\begin{array}{c} R_2 \\ R_3 \\ | \\ Y-CH-(CH_2)_n-CH-X-R_1 \end{array} \quad (I)$$

| Compound No. | R₁ | R₂ | R₃ | R₄ | R₅ | R₆ | Position of R₅/R₆ | X | Y | Z | m | n | Physical constant |
|---|---|---|---|---|---|---|---|---|---|---|---|---|---|
| 119 | pyridyl | H | Cl | H | H | H | 4- | O | S | O | 0 | 0 | |
| 120 | pyridyl | H | H | H | H | H | 3- | O | O | O | 0 | 0 | $n_D^{26.5}$ 1.5923 |
| 121 | pyridyl | H | H | H | 4-F | H | 3- | O | O | O | 0 | 0 | $n_D^{23.5}$ 1.5788 |
| 122 | pyridyl | H | H | H | 3-F | H | 3- | O | O | O | 0 | 0 | $n_D^{23.5}$ 1.5789 |
| 123 | pyridyl | H | H | H | 3-F | H | 3- | O | O | O | 0 | 0 | $n_D^{23.0}$ 1.5807 |
| 124 | pyridyl | H | H | H | 4-CH₃ | H | 3- | O | O | O | 0 | 0 | $n_D^{22.5}$ 1.5873 |

TABLE 1-continued
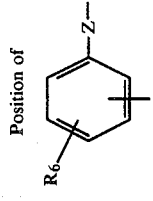
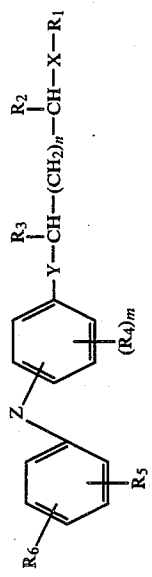
| Compound No. | R₁ | R₂ | R₃ | R₄ | R₅ | R₆ | Position of R₅ | X | Y | Z | m | n | Physical constant |
|---|---|---|---|---|---|---|---|---|---|---|---|---|---|
| 125 | (S,N thiazole) | H | H | H | 4-CH₃ | H | 3- | O | O | O | 0 | 0 | $n_D^{23.0}$ 1.5950 |
| 126 | (N,N pyrimidine) | H | H | H | 2-CH₃ | H | 3- | O | O | O | 0 | 0 | $n_D^{24.5}$ 1.5865 |
| 127 | (S,N thiazole) | H | H | H | 4-F | H | 3- | O | O | O | 0 | 0 | $n_D^{24.5}$ 1.5820 |
| 128 | (S,N thiazole) | H | H | H | 3-F | H | 3- | O | O | O | 0 | 0 | $n_D^{23.5}$ 1.5834 |
| 129 | (S,N thiazole) | H | H | H | 2-F | H | 3- | O | O | O | 0 | 0 | $n_D^{22.5}$ 1.5819 |
| 130 | (N pyridine) | CH₃ | H | H | H | H | 3- | O | O | O | 0 | 0 | $n_D^{25.0}$ 1.5813 |

TABLE 1-continued
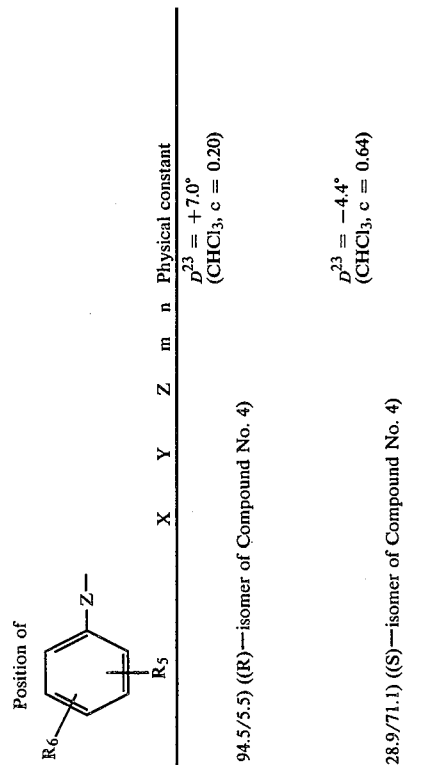
| Compound No. | R1 | R2 | R3 | R4 | R5 | R6 | X | Y | Z | m | n | Physical constant |
|---|---|---|---|---|---|---|---|---|---|---|---|---|
| 131 | (R/S = 94.5/5.5) ((R)—isomer of Compound No. 4) | | | | | | | | | | | $D^{23} = +7.0°$ (CHCl$_3$, c = 0.20) |
| 132 | (R/S = 28.9/71.1) ((S)—isomer of Compound No. 4) | | | | | | | | | | | $D^{23} = -4.4°$ (CHCl$_3$, c = 0.64) |
Note:
*In regard to Y.

TABLE 2

Structure: 3-F, 5-R₄''-phenyl-O-(para-phenylene)-O-CH(R₃'')-CH(R₂'')-R₁''

| Compound No. | R₁'' | R₂'' | R₃'' | R₄'' | Physical constant |
|---|---|---|---|---|---|
| 133 | \[3,5-difluorophenyl-O-phenyl-OCH₃ group spanning R₁''–R₄''\] | | | | $n_D^{29.5}$ 1.5364 |
| 134 | \[3,5-difluorophenyl-O-phenyl-OH group spanning R₁''–R₄''\] | | | | $n_D^{29.5}$ 1.5538 |
| 135 | OH | H | H | F | $n_D^{29.0}$ 1.5476 |
| 136 | OH | H | CH₃ | F | $n_D^{28.0}$ 1.5331 |
| 137 | OH | CH₃ | H | F | $n_D^{29.5}$ 1.5359 |
| 138 | Br | H | H | F | $n_D^{25.5}$ 1.5589 |
| 139 | Br | H | CH₃ | F | $n_D^{28.5}$ 1.5459 |
| 140 | Br | CH₃ | H | F | $n_D^{26.5}$ 1.5473 |
| 141 | OSO₂-C₆H₄-CH₃ (p-tolyl) | H | H | F | $n_D^{27.0}$ 1.5621 |
| 142 | OSO₂-C₆H₄-CH₃ (p-tolyl) | H | CH₃ | F | $n_D^{27.5}$ 1.5490 |
| 143 | OSO₂-C₆H₄-CH₃ (p-tolyl) | CH₃ | H | F | $n_D^{29.0}$ 1.5508 |
| 144 | OSO₂CH₃ | H | H | F | $n_D^{27.5}$ 1.4846 |
| 145 | OSO₂CH₃ | H | CH₃ | F | $n_D^{28.0}$ 1.4715 |
| 146 | OSO₂CH₃ | CH₃ | H | F | $n_D^{26.5}$ 1.4732 |
| 147 | OH | H | H | H | $n_D^{21.5}$ 1.4629 |
| 148 | OH | H | CH₃ | H | M.P. 40–44° C. |
| 149 | OH | CH₃ | H | H | M.P. 44.9° C. |
| 150 | Br | H | H | H | $n_D^{21.5}$ 1.5757 |
| 151 | Br | H | CH₃ | H | $n_D^{21.5}$ 1.5649 |
| 152 | Br | CH₃ | H | H | $n_D^{21.5}$ 1.5632 |

TABLE 3

| Compound No. | Structure | Physical constant |
|---|---|---|
| 153 | phenyl-O-(p-phenylene)-O-CH₂-C*(CH₃)(H)(OH), (S)-isomer | $[\alpha]_D^{23} = +18.5°$ (CHCl₃, c = 1) ee.: 96.3% |

TABLE 3-continued

| Compound No. | Structure | Physical constant |
|---|---|---|
| 154 | (structure: phenyl-O-phenyl-O-CH₂-C(CH₃)(H)(OH) with triple bond, (R)-isomer) | $[\alpha]_D^{23} = -19.1°$ (CHCl₃, c = 1) ee.: 99.4% |
| 155 | (structure: phenyl-O-phenyl-O-C(CH₃)(H)(CH₂OH) with triple bond, (S)-isomer) | $[\alpha]_D^{23} = +23.1°$ (CHCl₃, c = 0.39) ee.: 42.2% |
| 156 | (structure: phenyl-O-phenyl-O-C(CH₃)(H)(CH₂OH), (R)-isomer) | $[\alpha]_D^{23} = +48.7°$ (CHCl₃, c = 0.38) ee.: 89.7% |

On the application of the nitrogen-containing heterocyclic compounds (I) as insecticidal agents, they may be used as such or, preferably, in the form of an appropriate composition such as emulsifiable concentrates, dusts, granules, wettable powders and fine granules. The content of the nitrogen-containing heterocyclic compound (I) in such composition is usually from about 0.1 to 99.9% by weight, preferably from about 2.0 to 80.0% by weight.

The composition can be formulated in a per se conventional manner by mixing at least one of the nitrogen-containing heterocyclic compounds (I) with an appropriate solid or liquid carrier(s) or diluent(s). An appropriate adjuvant(s) (e.g. surfactants, adherents, dispersants, stabilizers) may be admixed therein for improving the dispersibility and other properties of the active ingredient on use.

Examples of the solid carriers or diluents are clays (e.g. kaolin, bentonite, fuller's earth, pyrophyllite, sericite), talcs, other inorganic materials (e.g. hydrated silica, pumice, diatomaceous earth, sulfur powder, active carbon) in fine powders or powdery form.

Examples of the liquid carriers or diluents are alcohols (e.g. methanol, ethanol), ketones (e.g. acetone, methyl ethyl ketone), ethers (e.g. diethyl ether, dioxane, cellosolve, tetrahydrofuran), aromatic hydrocarbons (e.g. benzene, toluene, xylene, methylnaphthalene), aliphatic hydrocarbons (e.g. gasoline, kerosene, lamp oil), esters, nitriles, acid amides (e.g. dimethylformamide, dimethylacetamide), halogenated hydrocarbons (e.g. dichloroethane, trichloroethylene, carbon tetrachloride, etc.

Examples of the surfactants are alkylsulfates, alkylsulfonates, alkylarylsulfonates, polyethylene glycol ethers, polyhydric alcohol esters, etc. Examples of the adherents and dispersants may include casein, gelatin, starch powder, CMC (carboxymethyl cellulose), gum arabic, alginic acid, ligninsulfonate, bentonite, molasses, polyvinyl alcohol, pine oil and agar. As the stabilizers, there may be used PAP (isopropyl acid phosphates mixture), TCP (tricresyl phosphate), tolu oil, epoxydized oil, various surfactants, various fatty acids and their esters, etc.

In addition, the said composition may contain insecticides, insect growth inhibitors, acaricides, nematocides, fungicides, herbicides, plant growth regulators, fertilizers, soil improvers, etc. Particularly when employed in conjunction with conventional insecticides, a broad spectrum of activity or a more immediate effect on very heterogeneous populations is provided. Examples of the insecticides include organic phosphorus compounds (e.g. fenitrothion (O,O-dimethyl-O-(3-methyl-4-nitrophenyl)phosphorothioate), malathion (S-[1,2-bis(ethoxycarbonyl)ethyl] O,O-dimethylphosphorothioate), dimethoate (O,O-dimethyl-S-(N-methylcarbamoylmethyl)phosphorodithioate), salithion (2-methoxy-4H-1,3,2-benzdioxaphosphorin-2-sulfide), diazinon (O,O-diethyl-O-(2-isopropyl-6-methyl-4-pyrimydinyl)phosphorothioate), dipterex (2,2,2-trichloro-1-hydroxyethyl-O,O-dimethylphosphonate), dichlorvos (O-(2,2-dichlorovinyl)-O,O-dimethylphosphate), etc.), carbamate compounds (e.g. MPMC (3,4-dimethylphenyl N-methylcarbamate), MTMC (m-tolyl N-methylcarbamate), BPMC (2-sec-butylphenyl N-methylcarbamate), carbaryl (1-naphthyl N-methylcarbamate), etc.) and pyrethroid compounds (e.g. resmethrin (5-benzyl-3-furylmethyl-d,l-cis,trans-chrysanthemate), permethrin (3-phenoxybenzyl-d,l-cis,trans-3-(2,2-dichlorovinyl)-2,2-dimethylcyclopropanecarboxylate), fenvalerate (α-cyano-m-phenoxybenzyl α-isopropyl-p-chlorophenylacetate), etc.).

The nitrogen-containing heterocyclic compounds (I) of the invention formulated into an appropriate composition may be applied in a suitable application method such as spraying, smoking, soil treatment, soil surface treatment or in combination with animal feed.

Some practical embodiments of the composition for the control of insects according to the invention are illustratively shown in the following Formulation Examples wherein % and part(s) are by weight.

FORMULATION EXAMPLE 1

Each of Compound Nos. 1 to 132 (20 parts), an emulsifier (a mixture of polyoxyethylene-styrenated phenyl ether, polyoxyethylene-styrenated phenyl ether polymer and an alkylarylsulfonate) (20 parts) and xylene (60 parts) are mixed well to make an emulsifiable concentrate.

FORMULATION EXAMPLE 2

Each of Compound Nos. 1 to 132 (20 parts) and an emulsifier (sodium laurylsulfate) (5 parts) are mixed well, and diatomaceous earth (300 mesh) (75 parts) is added thereto, and the resultant mixture is mixed well in a pulverizer to make a wettable powder.

FORMULATION EXAMPLE 3

Each of Compound Nos. 1, 3, 12 or 46 (3 parts) is dissolved in acetone (20 parts), talc (300 mesh) (97 parts) is added thereto, and the resultant mixture is mixed well in a pulverizer. Then, acetone is eliminated by evaporation to give a dust.

FORMULATION EXAMPLE 4

Each of Compound Nos. 1 or 12 (5 parts), a dispersant (calcium ligninsulfonate) (2 parts) and clay (93 parts) are mixed well in a pulverizer. To the resultant mixture, water is added in an amount of 10%, and the resulting mixture is kneaded well and granulated by the aid of a granulator, followed by drying to give granules.

FORMULATION EXAMPLE 5

Compound No. 3 (2 parts), a dispersant (calcium lingninsulfonate) (2 parts) and clay (96 parts) are mixed well in a pulverizer. Water is added to the resultant mixture in an amount of 10%. The resulting mixture is mixed well and granulated by the aid of a granulator, followed by air-drying to give fine granules.

FORMULATION EXAMPLE 6

Each of Compound Nos. 1 to 132 (10 parts), resmethrin ((20 parts), an emulsifier (a mixture of polyoxyethylene-styrenated phenyl ether, polyoxyethylene-styrenated phenyl ether polymer and an alkylarylsulfonate) (20 parts) and xylene (50 parts) are mixed well to make an emulsifiable concentrate.

FORMULATION EXAMPLE 7

Each of Compound Nos. 1 to 132 (10 parts), fenitrothion (20 parts) and an emulsifier (sodium laurylsulfate) (5 parts) are mixed well, and diatomaceous earth (300 mesh), (65 parts) is added thereto, and the resultant mixture is mixed well in a pulverizer to make a wettable powder.

The following Examples show some typical test data indicating the excellent insect control activity of the nitrogen-containing heterocylic compounds (I). The compounds used for comparison are as follows:

| Compound No. | Chemical structure | Remarks |
|---|---|---|
| A | 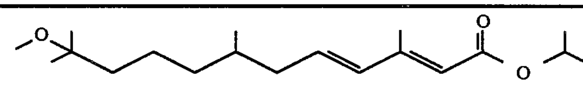 | Known as "methoprene"; U.S. Pat. Nos. 3,904,662 & 3,912,815 |
| B | 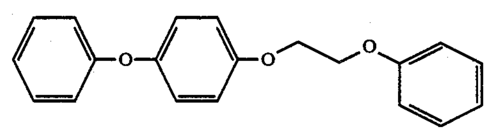 | Compound disclosed in Japanese Pat. Publn. (unexamined) No. 157522/1975 |
| C | 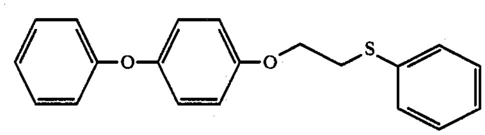 | Compound disclosed in DT-OS 2,616,755 |
| D | 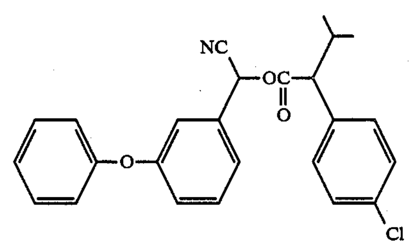 | Known as "fenvalerate" |
| E | $(CH_3O)_2P(=S)-O-C_6H_3(CH_3)-NO_2$ | Known as "fenitrothion" |

TEST EXAMPLE 1

Pupae of wax moth (*Galleria mellonella*) were collected within 20 hours from the pupation. According to the Schneiderman's method (J. Insect Physiol., 11, 1641 (1965)), a puncture of about 1 mm² was made in the right side of the thoracic dorsum of each pupa, and the wound was sealed with a designed amount of the test compound dissolved in a mixture of paraffin wax and peanut oil. The medicated pupae were kept at 28° C. in a pyrostat. The pupal cuticle at the medicated part was peeled off before emergence, and observation was made to examine the formation of the pupal cuticle, from which the average rate of reaction to the test compound was determined, and the dose of the test compound for 50% inhibition of the metamorphosis (ID$_{50}$) was calculated. The results are shown in Table 4.

TABLE 4

| Test compound No. | ID$_{50}$ (μg/pupa) |
|---|---|
| 1 | <0.001 |
| A | 2.2 |
| B | >1 |
| C | >1 |

TEST EXAMPLE 2

An emulsifiable concentrate prepared according to Formulation Example 1 was diluted with water to make a 400 fold dilution. The dilution (0.7 ml) was added to 100 ml of distilled water. Last instar larvae of common mosquito (*Culex pipiens pallens*) were released therein and reared for 7 day until their emergence. The rate of emergence was observed (two replications). The results are shown in Table 5.

TABLE 5

| Test compound No. | Concentration (ppm) | Rate of emergence (%) |
|---|---|---|
| 1 | 3.5 | 0 |
| 2 | 3.5 | 0 |
| 3 | 3.5 | 0 |
| 4 | 3.5 | 0 |
| 5 | 3.5 | 0 |
| 6 | 3.5 | 0 |
| 7 | 3.5 | 0 |
| 8 | 3.5 | 0 |
| 9 | 3.5 | 0 |
| 10 | 3.5 | 0 |
| 11 | 3.5 | 0 |
| 12 | 3.5 | 0 |
| 13 | 3.5 | 0 |
| 14 | 3.5 | 0 |
| 15 | 3.5 | 0 |
| 16 | 3.5 | 0 |
| 17 | 3.5 | 0 |
| 18 | 3.5 | 0 |
| 19 | 3.5 | 0 |
| 20 | 3.5 | 0 |
| 21 | 3.5 | 0 |
| 22 | 3.5 | 0 |
| 23 | 3.5 | 0 |
| 24 | 3.5 | 0 |
| 25 | 3.5 | 0 |
| 26 | 3.5 | 0 |
| 27 | 3.5 | 0 |
| 28 | 3.5 | 0 |
| 29 | 3.5 | 0 |
| 30 | 3.5 | 0 |
| 31 | 3.5 | 0 |
| 32 | 3.5 | 0 |
| 33 | 3.5 | 0 |
| 34 | 3.5 | 0 |
| 35 | 3.5 | 0 |
| 36 | 3.5 | 0 |
| 37 | 3.5 | 0 |
| 38 | 3.5 | 0 |
| 39 | 3.5 | 0 |
| 40 | 3.5 | 0 |
| 41 | 3.5 | 0 |
| 42 | 3.5 | 0 |
| 43 | 3.5 | 0 |
| 44 | 3.5 | 0 |
| 45 | 3.5 | 0 |
| 46 | 3.5 | 0 |
| 47 | 3.5 | 0 |
| 48 | 3.5 | 0 |
| 49 | 3.5 | 0 |
| 50 | 3.5 | 0 |
| 51 | 3.5 | 0 |
| 52 | 3.5 | 0 |
| 53 | 3.5 | 0 |
| 54 | 3.5 | 0 |
| 55 | 3.5 | 0 |
| 56 | 3.5 | 0 |
| 57 | 3.5 | 0 |
| 58 | 3.5 | 0 |
| 59 | 3.5 | 0 |
| 60 | 3.5 | 0 |
| 61 | 3.5 | 0 |
| 62 | 3.5 | 0 |
| 63 | 3.5 | 0 |
| 64 | 3.5 | 0 |
| 65 | 3.5 | 0 |
| 66 | 3.5 | 0 |
| 67 | 3.5 | 0 |
| 68 | 3.5 | 0 |
| 69 | 3.5 | 0 |
| 70 | 3.5 | 0 |
| 71 | 3.5 | 0 |
| 72 | 3.5 | 0 |
| 73 | 3.5 | 0 |
| 74 | 3.5 | 0 |
| 75 | 3.5 | 0 |
| 76 | 3.5 | 0 |
| 77 | 3.5 | 0 |
| 78 | 3.5 | 0 |
| 79 | 3.5 | 0 |
| 80 | 3.5 | 0 |
| 81 | 3.5 | 0 |
| 82 | 3.5 | 0 |
| 83 | 3.5 | 0 |
| 84 | 3.5 | 0 |
| 85 | 3.5 | 0 |
| 86 | 3.5 | 0 |
| 87 | 3.5 | 0 |
| 88 | 3.5 | 0 |
| 89 | 3.5 | 0 |
| 90 | 3.5 | 0 |
| 91 | 3.5 | 0 |
| 92 | 3.5 | 0 |
| 93 | 3.5 | 0 |
| 94 | 3.5 | 0 |
| 95 | 3.5 | 0 |
| 96 | 3.5 | 0 |
| 97 | 3.5 | 0 |
| 98 | 3.5 | 0 |
| 99 | 3.5 | 0 |
| 100 | 3.5 | 0 |
| 101 | 3.5 | 0 |
| 102 | 3.5 | 0 |
| 103 | 3.5 | 0 |
| 104 | 3.5 | 0 |
| 105 | 3.5 | 0 |
| 106 | 3.5 | 0 |
| 107 | 3.5 | 0 |
| 108 | 3.5 | 0 |
| 109 | 3.5 | 0 |
| 110 | 3.5 | 0 |
| 111 | 3.5 | 0 |
| 112 | 3.5 | 0 |
| 113 | 3.5 | 0 |
| 114 | 3.5 | 0 |
| 115 | 3.5 | 0 |
| 116 | 3.5 | 0 |
| 117 | 3.5 | 0 |
| 118 | 3.5 | 0 |
| 119 | 3.5 | 0 |
| 120 | 3.5 | 0 |
| 121 | 3.5 | 0 |
| 122 | 3.5 | 0 |
| 123 | 3.5 | 0 |
| 124 | 3.5 | 0 |
| 125 | 3.5 | 0 |
| 127 | 3.5 | 0 |
| 129 | 3.5 | 0 |
| 130 | 3.5 | 0 |
| 131 | 3.5 | 0 |
| 132 | 3.5 | 0 |
| A | 3.5 | 0 |
| Untreated | — | 90 |

TEST EXAMPLE 3

An emulsifiable concentrate prepared according to Formulation Example 1 was diluted with water to a designed dilution. The dilution (0.5 ml) was added to 100 ml of distilled water. Twenty last instar larvae of common mosquito (*Culex pipiens pallens*) were released therein and reared for 7 days until their emergence. The 50% emergence inhibition concentration ($IC_{50}$) (ppm) was determined (two replications). The results are shown in Table 6 wherein $PI_{50}$ corresponds to $-\log IC_{50}$.

TABLE 6

| Test Compound No. | $PI_{50}$ |
|---|---|
| 1 | 4.3 |
| 3 | 4.2 |
| 6 | 4.6 |
| 19 | 3.9 |
| 20 | 4.4 |
| 23 | 4.4 |
| 46 | 3.8 |
| 49 | 5.2 |
| 89 | 4.4 |
| 95 | 4.2 |
| 97 | 4.7 |
| 124 | 4.1 |
| 125 | 4.1 |
| A | 3.7 |
| B | 1.1 |
| C | 1.6 |

TEST EXAMPLE 4

Powdered animal feed (2 g) was thoroughly mixed with bran (14 g). An emulsifiable concentrate prepared according to Formulation Example 1 was diluted with water to a designed concentration and the dilution (28 ml) was added to the above mixture. The resultant mixture was stirred well to make an artificial culture. Thirty larvae of housefly (*Musca domestica*) were reared therein until their pupation. The obtained pupae were placed into a plastic cup, and the rate of emergence was determined. According to the following equation, the emergence inhibition (%) was calculated:

$$\text{Emergence inhibition \%} = \left(1 - \frac{\text{Rate of emergence in treated plot}}{\text{Rate of emergence in untreated plot}}\right) \times 100$$

The results are shown in Table 7.

TABLE 7

| Test compound No. | Emergence inhibition (%) | | |
|---|---|---|---|
| | 3 ppm | 1 ppm | 0.3 ppm |
| 1 | 100 | 100 | 100 |
| 2 | 100 | 100 | 52 |
| 3 | 100 | 100 | 100 |
| 4 | 100 | 100 | 100 |
| 5 | 100 | 100 | 100 |
| 6 | 100 | 100 | 100 |
| 10 | 100 | 89 | 22 |
| 12 | 100 | 100 | 100 |
| 15 | 100 | 100 | 100 |
| 19 | 100 | 100 | 100 |
| 28 | 78 | 51 | 0 |
| 31 | 100 | 100 | 100 |
| 32 | 96 | 66 | 0 |
| 33 | 100 | 92 | 34 |
| 34 | 79 | 23 | 0 |
| 35 | 97 | 97 | 80 |
| 37 | 100 | 100 | 100 |
| 38 | 97 | 93 | 77 |
| 39 | 100 | 100 | 97 |
| 46 | 100 | 100 | 100 |
| 47 | 100 | 100 | 100 |
| 49 | 97 | 62 | 8 |
| 50 | 100 | 95 | 23 |
| 51 | 100 | 68 | 2 |
| 61 | 100 | 100 | 100 |
| 62 | 100 | 100 | 89 |
| 63 | 100 | 100 | 100 |
| 64 | 100 | 100 | 100 |
| 66 | 100 | 100 | 100 |
| 67 | 100 | 100 | 100 |
| 68 | 100 | 100 | 89 |
| 69 | 100 | 100 | 100 |
| 71 | 100 | 100 | 100 |
| 72 | 100 | 100 | 100 |
| 73 | 100 | 100 | 96 |
| 74 | 100 | 100 | 83 |
| 75 | 100 | 100 | 95 |
| 76 | 100 | 100 | 100 |
| 77 | 100 | 100 | 100 |
| 78 | 100 | 100 | 100 |
| 79 | 100 | 100 | 95 |
| 82 | 100 | 89 | 41 |
| 83 | 100 | 92 | 57 |
| 84 | 100 | 67 | 16 |
| 85 | 100 | 100 | 97 |
| 97 | 100 | 100 | 85 |
| 98 | 100 | 100 | 96 |
| 99 | 100 | 100 | 92 |
| 100 | 100 | 100 | 32 |
| 101 | 100 | 100 | 40 |
| 102 | 100 | 100 | 100 |
| 103 | 100 | 100 | 92 |
| 120 | 100 | 79 | 46 |
| 122 | 100 | 47 | 7 |
| 131 | 100 | 100 | 100 |
| 132 | 100 | 100 | 100 |
| A | 60 | 13 | 2 |
| B | 36 | 15 | 0 |
| C | 0 | 0 | 0 |

TEST EXAMPLE 5

Adults of female carmine spider mites (*Tetranychus cinnabarinus*) were permitted to live on four leaves (10 mites per leaf) of kidney bean after 5 days of its plantation in the pots, and the adults were kept at 27° C. in a pyrostat. After 6 days, a 400 fold dilution (500 ppm) of the emulsifiable concentration prepared according to Formulation Example 1 was sprayed over the pots placed on a turn table at a spray volume of 10 ml per pot, and also 2 ml of the dilution was applied to the soil in each pot. Eight days thereafter, the number of the adults were counted and the insect control activity was judged according to the following criteria:

++: 0 to 9 adults living on a leaf
+: 10 to 30 adults living on a leaf
−: more than 31 adults living on a leaf The results are shown in Table 8.

TABLE 8

| Test Compound No. | Judgment |
|---|---|
| 46 | + |
| 80 | ++ |
| 126 | + |
| 128 | ++ |
| B | − |
| C | − |

TABLE 8-continued

| Test Compound No. | Judgment |
|---|---|
| Untreated | — |

TEST EXAMPLE 6

Each fifty adults of male and female houseflies (*Musca domestica*) were put in a cage. Separately, powdered feed (2 g), bran (14 g) and water (28 ml) were thoroughly mixed to make an artificial culture and thirty 4-day-old larvae of housefly were reared therein. A 20% emulsifiable concentrate of Compound No. 3 prepared according to Formulation Example 1 and diluted with water as well as its mixture with Compound D and Compound E was sprayed to each of the cage and the culture at a spray volume of 20 ml. After the spraying, the culture was put in the cage, and the numbers of the adults within the cage were observed with lapse of days and evaluated in terms of "corrected density index", which was calculated according to the following equation:

$$\text{Corrected density index} = \frac{\text{Number of adult before treatment in untreated plot} \times \text{Number of adult after treatment in treated plot}}{\text{Number of adult after treatment in untreated plot} \times \text{Number of adult before treatment in treated plot}} \times 100$$

The results are shown in Table 9.

TABLE 9

| Compound No. | Concentration (ppm) | Corrected density index | | | | |
|---|---|---|---|---|---|---|
| | | 1 day | 2 days | 5 days | 16 days | 22 days |
| 3 | 5 | 98 | 98 | 99 | 3 | 2 |
| D | 10 | 25 | 24 | 23 | 64 | 81 |
| E | 10 | 30 | 22 | 22 | 71 | 80 |
| 3/D | 5/10 | 34 | 29 | 25 | 4 | 2 |
| 3/E | 5/10 | 33 | 31 | 30 | 2 | 1 |

TEST EXAMPLE 7

An emulsifiable concentrate prepared according to Formulation Example 1 was diluted with water to a designed concentration. The resultant dilution (50 ml) was added to feed for domestic fowl (100 g) and thoroughly mixed. The thus obtained mixture was fed to groups of fowls (each group consisting of three animals) at a daily dose of 100 g/fowl for 2 days, whereupon their droppings were collected. Two hundred eggs of housefly. (*Musca domestica*) were incubated in the droppings until their pupation. The obtained pupae were placed into another container, and the 50% emergence inhibition concentration (IC$_{50}$) was examined. The results are shown in Table 10.

TABLE 10

| Test Compound No. | IC$_{50}$ (ppm) |
|---|---|
| 1 | 0.69 |
| 3 | 0.24 |
| A | 32 |

What is claimed is:

1. A nitrogen-containing heterocyclic compound of the formula:

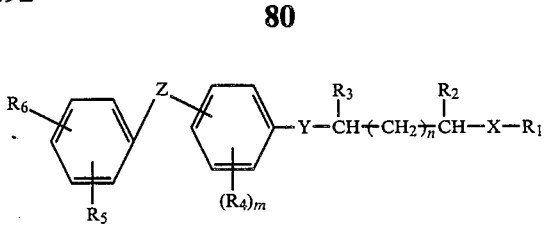

wherein
$R_1$ is one of the following groups:

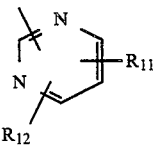

or

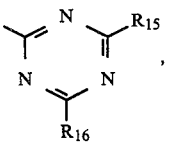

in which $R_{11}$, $R_{12}$, $R_{15}$ and $R_{16}$ are, the same or different, each a hydrogen atom, a halogen atom, a $C_1$-$C_4$ alkyl group, a $C_1$-$C_4$ alkoxy group, a $C_1$-$C_4$ alkylthio group, a trifluoromethyl group or a nitro group;

$R_2$ and $R_3$ are, the same or different, each a hydrogen atom, a halogen atom or a methyl group;

$R_4$ is a halogen atom or a methyl group;

$R_5$ and $R_6$ are, the same or different, each a hydrogen atom, a halogen atom, a $C_1$-$C_4$ alkyl group, a $C_1$-$C_4$ alkoxy group, a $C_1$-$C_4$ haloalkyl group or a $C_1$-$C_4$ haloalkoxy group;

X, Y and Z are, the same or different, each an oxygen atom, a sulfur atom or a methylene group;

m is an integer of 0 to 4; and n is an integer of 0 to 2.

2. The nitrogen-containing heterocyclic compound according to claim 1, wherein:

$R_1$ is:

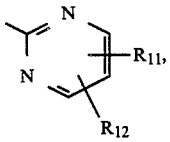

in which $R_{11}$ and $R_{12}$ are each a hydrogen atom or a fluorine atom;

$R_2$ and $R_3$ are, the same or different, each a hydrogen atom, a halogen atom or a methyl group;

$R_5$ and $R_6$ are, the same or different, each a hydrogen atom or a fluorine atom;

X is an oxygen atom or a sulfur atom;

Y is an oxygen atom;

Z is an oxygen atom or a methylene group; and m and n are each an integer of 0.

3. The nitrogen-containing heterocyclic compound according to claim 1, which is representable by the formula:

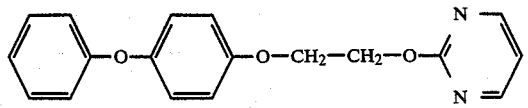

4. The nitrogen-containing heterocyclic compound according to claim 1, which is representabe by the formula:

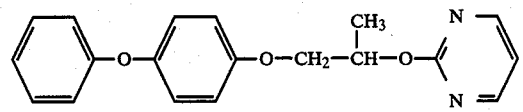

5. The nitrogen-containing heterocyclic compound according to claim 1, which is representable by the formula:

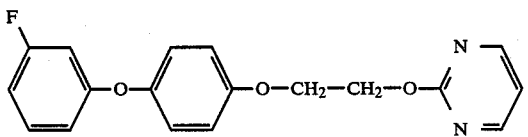

6. The nitrogen-containing heterocyclic compound according to claim 1, which is representable by the formula:

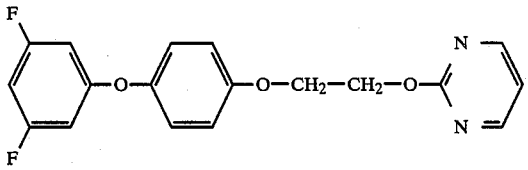

7. The nitrogen-containing heterocyclic compound according to claim 1, which is representable by the formula:

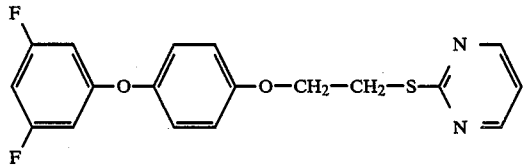

8. The nitrogen-containing heterocyclic compound according to claim 1, which is representable by the formula:

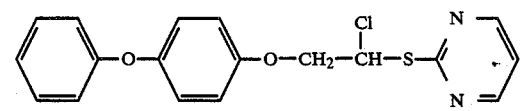

9. A composition for preventing or exterminating insects which comprises as an active ingredient an insecticidally effective amount of the compound according to claim 1, and an inert carrier or diluent.

10. A method for preventing or exterminating insects which comprises applying an insecticidally effective amount of the compound according to claim 1 to the insects.

11. The nitrogen-containing heterocyclic compound according to claim 1, which is representable by the formula:

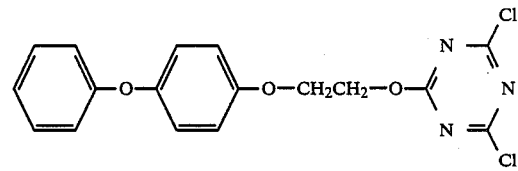

12. The nitrogen-containing heterocyclic compound according to claim 1, which is representable by the formula:

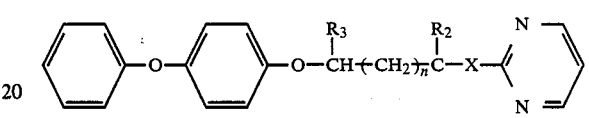

wherein $R_2$, $R_3$, X and n are each as defined in claim 1.

13. The nitrogen-containing heterocyclic compound according to claim 1, which is representable by the formula:

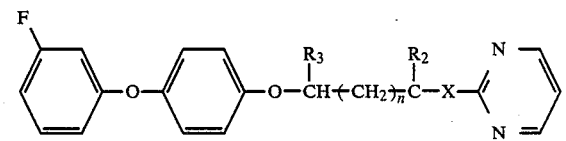

wherein $R_2$, $R_3$, X and n are each as defined in claim 1.

14. The nitrogen-containing heterocyclic compound according to claim 1, which is representable by the formula:

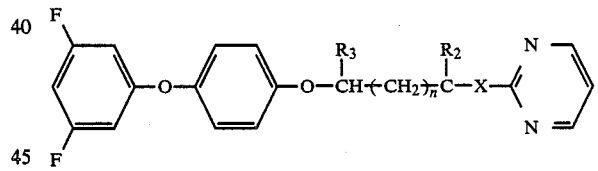

wherein $R_2$, $R_3$, X and n are each as defined in claim 1.

15. The nitrogen-containing heterocyclic compound according to claim 1, which is representable by the formula:

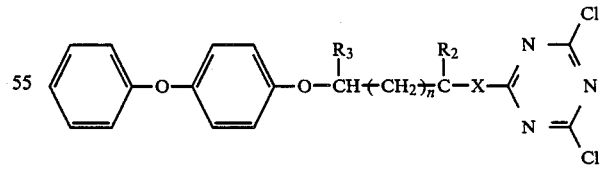

wherein $R_2$, $R_3$, X and n are each as defined in claim 1.

16. A composition for preventing or exterminating insects which comprises as an active ingredient an insecticidally effective amount of the compound according to claim 3, and an inert carrier or diluent.

17. A composition for preventing or exterminating insects which comprises as an active ingredient an insecticidally effective amount of the compound according to claim 4, and an inert carrier or diluent.

18. A composition for preventing or exterminating insects which comprises as an active ingredient an insecticidally effective amount of the compound according to claim 5, and an inert carrier or diluent.

19. A composition for preventing or exterminating insects which comprises as an active ingredient or insecticidally effective amount of the compound according to claim 6, and an inert carrier or diluent.

20. A composition for preventing or exterminating insects which comprises as an active ingredient an insecticidally effective amount of the compound according to claim 7, and an inert carrier or diluent.

21. A composition for preventing or exterminating insects which comprises as an active ingredient an insecticidally effective amount of the compound according to claim 8, and an inert carrier or diluent.

22. A composition for preventing or exterminating insects which comprises as an active ingredient an insecticidally effective amount of the compound according to claim 11, and an inert carrier or diluent.

23. A composition for preventing or exterminating insects which comprises as an active ingredient an insecticidally effective amount of the compound according to claim 12, and an inert carrier or diluent.

24. A composition for preventing or exterminating insects which comprises as an active ingredient an insecticidally effective amount of the compound according to claim 13, and an inert carrier or diluent.

25. A composition for preventing or exterminating insects which comprises as an active ingredient an insecticidally effective amount of the compound according to claim 14, and an inert carrier or diluent.

26. A composition for preventing or exterminating insects which comprises as an active ingredient an insecticidally effective amount of the compound according to claim 15, and an inert carrier or diluent.

27. A method for preventing or exterminating insects which comprises applying an insecticidally effective amount of the compound according to claim 3 to the insects.

28. A method for preventing or exterminating insects which comprises applying an insecticidally effective amount of the compound according to claim 4 to the insects.

29. A method for preventing or exterminating insects which comprises applying an insecticidally effective amount of the compound according to claim 5 to the insects.

30. A method for preventing or exterminating insects which comprises applying an insecticidally effective amount of the compound according to claim 6 to the insects.

31. A method for preventing or exterminating insects which comprises applying an insecticidally effective amount of the compound according to claim 7 to the insects.

32. A method for preventing or exterminating insects which comprises applying an insecticidally effective amount of the compound according to claim 8 to the insects.

33. A method for preventing or exterminating insects which comprises applying an insecticidally effective amount of the compound according to claim 11 to the insects.

34. A method for preventing or exterminating insects which comprises applying an insecticidally effective amount of the compound according to claim 12 to the insects.

35. A method for preventing or exterminating insects which comprises applying an insecticidally effective amount of the compound according to claim 13 to the insects.

36. A method for preventing or exterminating insects which comprises applying an insecticidally effective amount of the compound according to claim 14 to the insects.

37. A method for preventing or exterminating insects which comprises applying an insecticidally effective amount of the compound according to claim 15 to the insects.

* * * * *